US008691760B2

(12) United States Patent
Frenkel et al.

(10) Patent No.: US 8,691,760 B2
(45) Date of Patent: *Apr. 8, 2014

(54) PEPTIDES, PHARMACEUTICAL COMPOSITIONS COMPRISING SAME AND USES THEREOF

(75) Inventors: Dan Frenkel, Rechovot (IL); Adi Kopelevich, Holon (IL); Veronica Lifshitz, Petach-Tikva (IL); Tali Benromano, Tel-Aviv (IL); Nofit Borenstein, Ramat-Gan (IL)

(73) Assignee: Ramot at Tel-Aviv University, Tel-Aviv (IL)

( * ) Notice: Subject to any disclaimer, the term of this patent is extended or adjusted under 35 U.S.C. 154(b) by 65 days.

This patent is subject to a terminal disclaimer.

(21) Appl. No.: 13/147,406

(22) PCT Filed: Feb. 2, 2010

(86) PCT No.: PCT/IL2010/000093
§ 371 (c)(1),
(2), (4) Date: Oct. 11, 2011

(87) PCT Pub. No.: WO2010/086867
PCT Pub. Date: Aug. 5, 2010

(65) Prior Publication Data
US 2012/0028894 A1 Feb. 2, 2012

Related U.S. Application Data

(60) Provisional application No. 61/202,162, filed on Feb. 2, 2009.

(51) Int. Cl.
A61K 38/08 (2006.01)
A61K 38/16 (2006.01)
A61K 38/05 (2006.01)
A61K 38/10 (2006.01)
A61P 3/08 (2006.01)
A61P 3/10 (2006.01)
A61P 9/00 (2006.01)
A61P 25/00 (2006.01)
A61P 31/12 (2006.01)
C07K 14/00 (2006.01)
C07K 7/06 (2006.01)
C07K 7/08 (2006.01)

(52) U.S. Cl.
USPC ........... 514/6.9; 514/6.8; 514/20.8; 514/15.4; 514/17.7; 514/16.4; 514/3.7; 530/327; 530/326; 562/553; 206/438

(58) Field of Classification Search
IPC A61K 38/08,38/16, 38/05, 38/10; C07K 14/00, C07K 7/06, 7/08, 5/06; A61B 19/02
See application file for complete search history.

(56) References Cited

U.S. PATENT DOCUMENTS

| 5,824,319 A | 10/1998 | Vafai |
| 7,108,972 B2 | 9/2006 | Pena et al. |
| 2003/0104981 A1 | 6/2003 | Mandic |
| 2009/0088367 A1 | 4/2009 | Lipton et al. |
| 2009/0143275 A1 | 6/2009 | Pugia et al. |
| 2013/0130976 A1 | 5/2013 | Frenkel et al. |

FOREIGN PATENT DOCUMENTS

| CN | 1292798 | 4/2001 |
| CN | 1355813 | 6/2002 |
| CN | 101801412 | 8/2010 |
| WO | WO 99/35169 | 7/1999 |
| WO | WO 00/78805 | 12/2000 |
| WO | WO 03/102016 | 12/2003 |
| WO | WO 2006/128026 | 11/2006 |
| WO | WO 2008/156701 | 12/2008 |
| WO | WO 2010/086867 | 8/2010 |
| WO | WO 2010/123720 | 10/2010 |
| WO | WO 2012/017439 | 2/2012 |

OTHER PUBLICATIONS

Translation of Notification of Office Action Dated Jan. 28, 2013 From the State Intellectual Property Office of the People's Republic of China Re. Application No. 201080014546.2.
Translation of Search Report Dated Jan. 28, 2013 From the State Intellectual Property Office of the People's Republic of China Re. Application No. 201080014546.2.
International Preliminary Report on Patentability Dated Feb. 14, 2013 From the International Bureau of WIPO Re. Application No. PCT/IL2011/000638.
International Search Report and the Written Opinion Dated Mar. 13, 2012 From the International Searching Authority Re. Application No. PCT/IL2011/000638.
International Preliminary Report on Patentability Dated Aug. 11, 2011 From the International Bureau of WIPO Re. Application No. PCT/IL2010/000093.
International Search Report and the Written Opinion Dated Oct. 27, 2010 From the International Searching Authority Re: Application No. PCT/IL2010/000093.
Farris et al. "Insulin-Degrading Enzyme Regulates the Levels of Insulin, Amyloid β-Protein, and the β-Amyloid Precursor Protein Intracellular Domain In Vivo", Proc. Natl. Acad. Sci USA, 100(7): 4162-4167, Apr. 1, 2003.
Ghosh et al. "The Finland-United States Investigation of Non-Insulin-Dependent Diabetes Mellitus Genetics (FUSION) Study. I. An Autosomal Genome Scan for Genes That Predispose to Type 2 Diabetes", American Journal of Human Genetics, 67: 1174-1185, 2000.

(Continued)

Primary Examiner — Julie Ha
Assistant Examiner — Erinne Dabkowski

(57) ABSTRACT

Use of an isolated peptide comprising an amino acid sequence being no more than 25 amino acids in length, the amino acid sequence comprising at least one aspartate or a homolog thereof, the peptide having an Insulin-Degrading Enzyme (IDE) inhibitory activity, for the manufacture of a medicament identified for treating a disease selected from the group consisting of diabetes, obesity, hyperglycemia, retinal damage, renal failure, nerve damage, microvascular damage and varicella-zoster virus (VZV) infection is disclosed.

11 Claims, 16 Drawing Sheets
(9 of 16 Drawing Sheet(s) Filed in Color)

(56) References Cited

OTHER PUBLICATIONS

Li et al. "Insulin Degrading Enzyme is a Cellular Receptor Mediating Varicella-Zoster Virus Infection and Cell-to-Cell Spread", Cell, 127(2): 305-316, Oct. 20, 2006.

Meigs et al. "A Genome-Wide Scan for Loci Linked to Plasma Levels of Glucose and HbA1c in a Community-Based Sample of Caucasian Pedigrees. The Framingham Offspring Study", Diabetes, 51(3): 833-840, 2002.

Shen et al. "Structure of Human Insulin-Degrading Enzyme Reveal a New Substrate Recognition Mechanism", Nature, 443: 870-874, Oct. 19, 2006.

Simkin et al. "The Inactivation of Insulin by Tissue Extracts. III. The Effect of Force-Fed Diets on the Insulinase Activity of Rat Liver Extracts", Archives in Biochemistry, 24: 422-428, 1949.

Vinik et al. "Advances in Diabetes for the Millennium: New Treatments for Diabetic Neuropathies", Medscape General Medicine, MedGenMed, 6(3 Suppl.): 13, Aug. 17, 2004.

Wiltshire et al. "Evidence for Linkage of Stature to Chromosome 3p26 in a Large U.K. Family Data Set Ascertained fro Type 2 Diabetes", American Journal of Human Genetics, 70: 543-546, 2002.

Shen et al. "The Mg-Chelatase H Subunit is an Abscisic Acid Receptor", Nature, 443: 823-826, Oct. 19, 2006.

Communication Relating to the Results of the Partial International Search Dated Nov. 30, 2011 From the International Searching Authority Re. Application No. PCT/IL2011/000638.

Kurochkin et al. "Alzheimer's Beta-Amyloid Peptide Specifically Interacts With and is Degrade by Insulin Degrading Enzyme", FEBS Letters, XP025890466, 345(1): 33-37, May 23, 1994.

Official Action Dated Dec. 26, 2013 From the U.S. Patent and Trademark Office Re. U.S. Appl. No. 13/813,969.

Bennett et al. "An Insulin-Degrading Enzyme Inhibitor Decreases Amylin Degradation, Increases Amylin-Induced Cytoxicity, and Increases Amyloid Formation in Insulinoma Cell Cultures", Diabetes, 52: 2315-2320, Sep. 2003.

Cordes et al. "Nitric Oxide Inhibits Insulin-Degrading Enzyme Activity and Function Through S-Nitrosylation", Biochemical Pharmacology, 77: 1064-1073, 2009.

Leissring et al. "Designed Inhibitors of Insulin-Degrading Enzyme Regulate the Catabolism and Activity of Insulin", PLoS ONE, 5(5): e10504-1-e10504-13, May 2010.

Sriram et al. "Experimental Allergic Encephalomyelitis: A Misleading Model of Multiple Sclerosis", Annals of Neurology, 58(6): 939-945, Dec. 2005.

Steinman et al. "How to Successfully Apply Animal Studies in Experimental Allergic Encephalomyelitis to Research on Multiple Sclerosis", Annals of Neurology, 60(1): Jul. 12-21, 2006.

FIG. 2

```
Insulin    ------------EALY----LVCG------------  8 (SEQ ID NO. 1)
Amylin     ------------LANF----LVHSSNN---------- 11 (SEQ ID NO. 3)
Glucagon   ------------FVQW----LMN--------------  7 (SEQ ID NO. 4)
Amyloid    ------------KLVF----FAED-------------  8 (SEQ ID NO. 2)
VZV        ITNPVRASVLRYDDFHTDEDKLDTNSV          27 (SEQ ID NO. 5)
```

FIG. 3

1. ADT-1: VLRYDDFHTD (SEQ ID NO. 14) – Contains component from VZV
2. ADT-2: EALYDDLVCG (SEQ ID NO. 15) – Contains component from Insulin
3. ADT-3: LANFDDLVHSSNN (SEQ ID NO. 16) – Contains component from Amylin
4. ADT-4: FVQWDDLMN (SEQ ID NO. 17) – Contains component from Glucagon
5. ADT-5: KLVFDDFAED (SEQ ID NO. 18) – Contains component from Amyloid

FIG. 4

Insulin     FVNQ----    4  (SEQ ID NO. 6)
Amylin      KCNT----    4  (SEQ ID NO. 7)
Glucagon    HSQG----    4  (SEQ ID NO. 8)

VZV         ITNPVRAS    8  (SEQ ID NO. 9)

FIG. 5

1. ADT-21: ITNPGSGGSSVLRYDDFHTD (SEQ ID NO. 19)
2. ADT-22: FVNQGSGGSSEALYDDLVCG (SEQ ID NO. 20)
3. ADT-23: KCNTGSGGSSLANFDDLVHSSNN (SEQ ID NO. 21)
4. ADT-24: HSQGGSGGSSFVQWDDLMN (SEQ ID NO. 22)
5. ADT-25: DAEFGSGGSSKLVFDDFAED (SEQ ID NO. 23)

FIGs. 12A-C

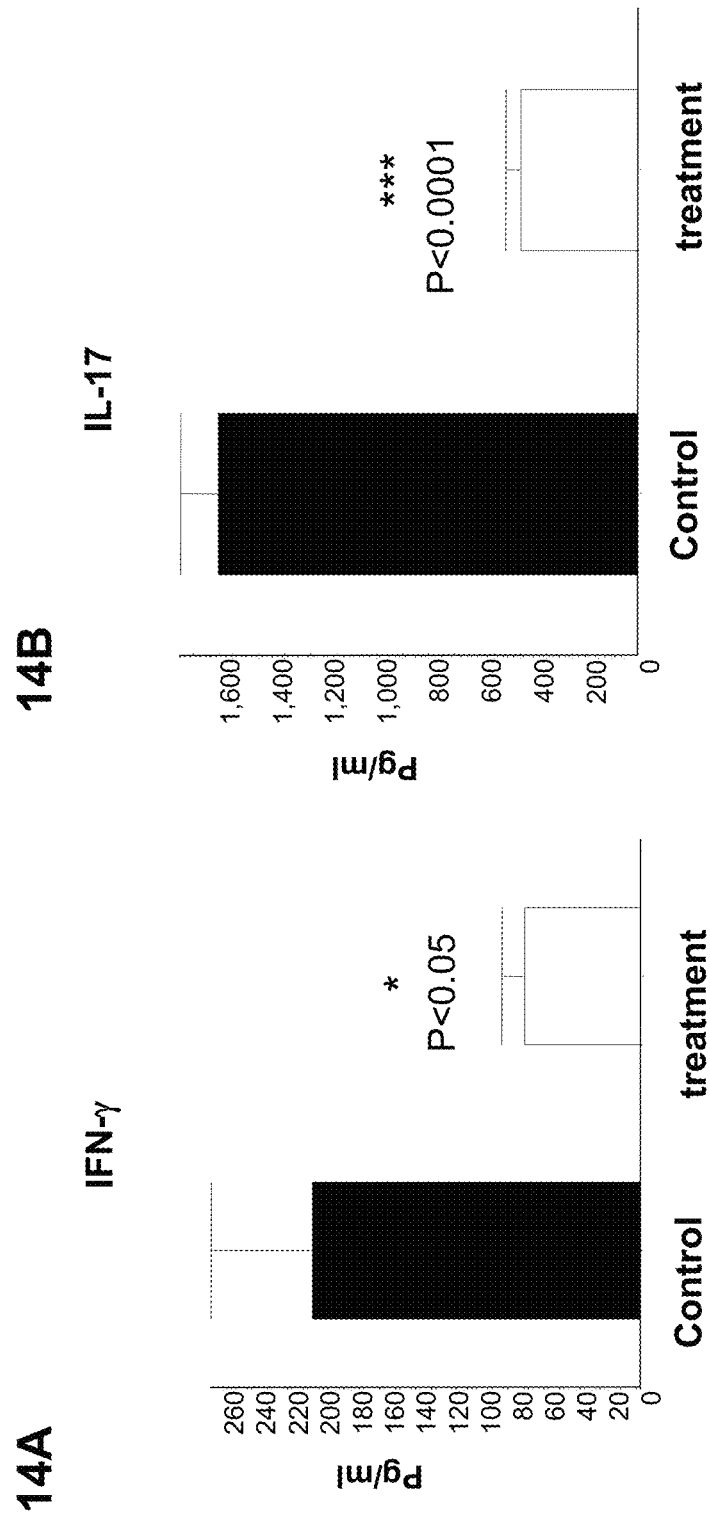
FIGs. 14A-B

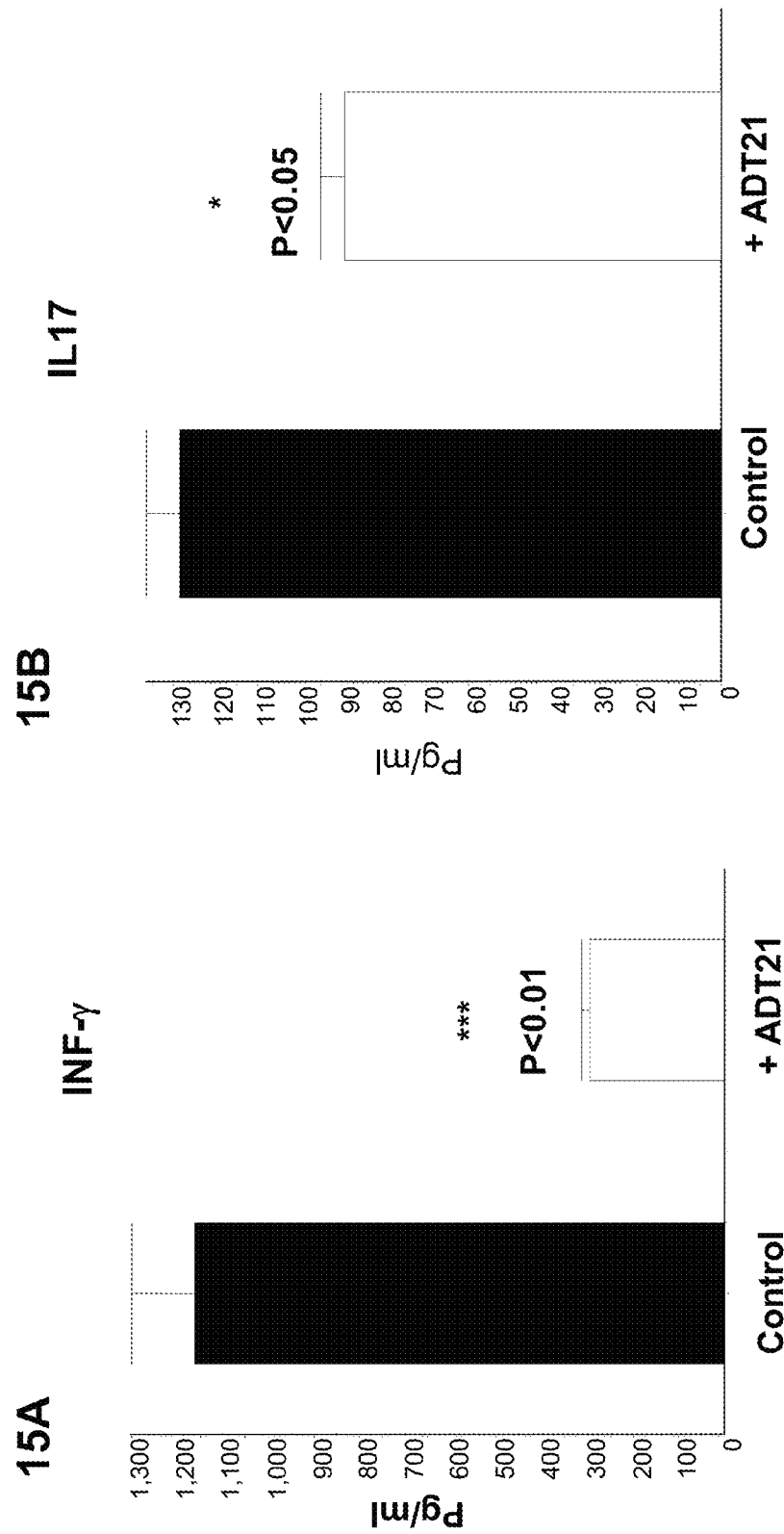
FIGs. 15A-B

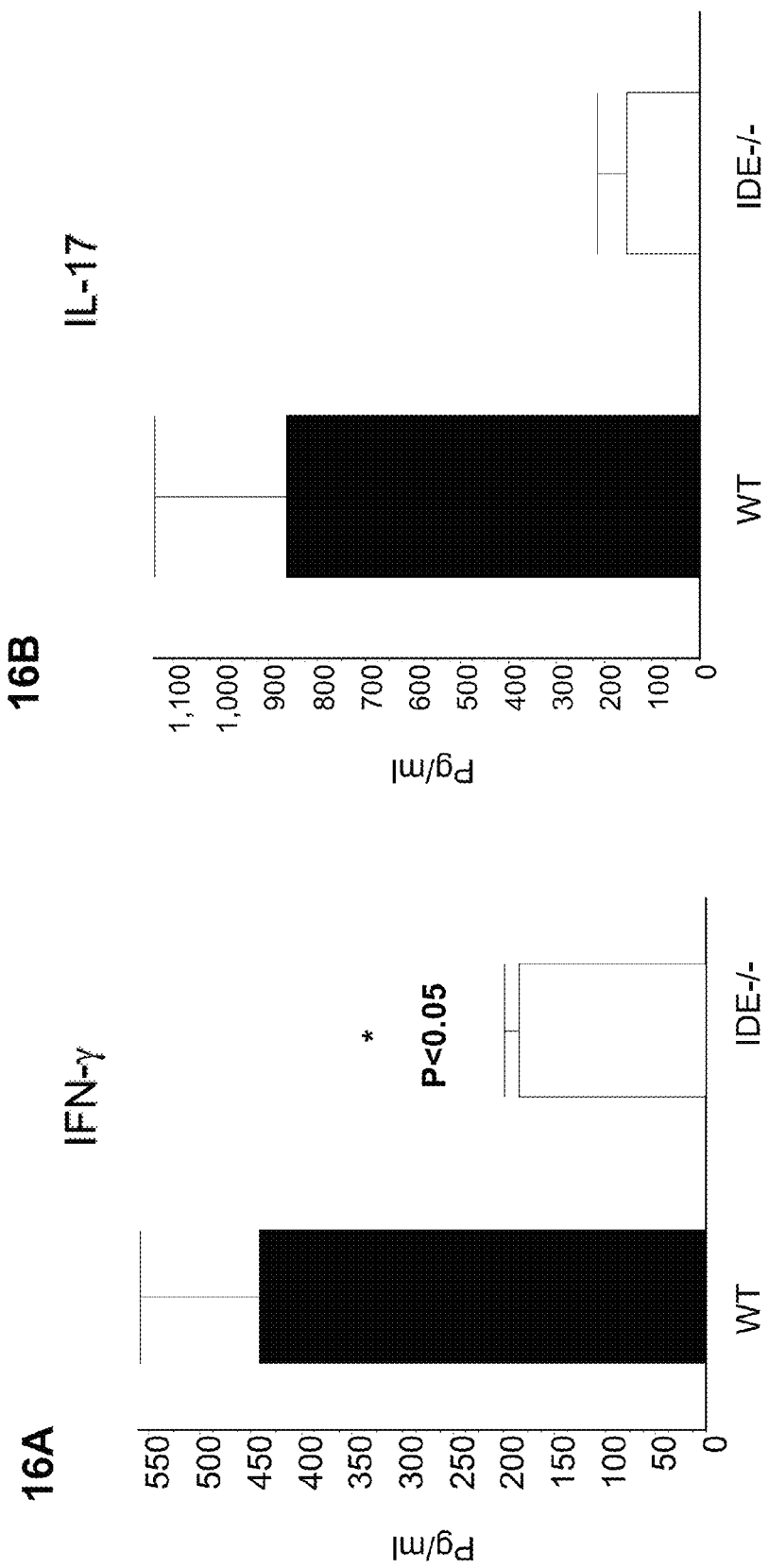

SEQUENCE LISTING

```
<160> NUMBER OF SEQ ID NOS: 88

<210> SEQ ID NO 1
<211> LENGTH: 8
<212> TYPE: PRT
<213> ORGANISM: Artificial sequence
<220> FEATURE:
<223> OTHER INFORMATION: A peptide sequence derived from Insulin B
      (37-44)

<400> SEQUENCE: 1

Glu Ala Leu Tyr Leu Val Cys Gly
1               5

<210> SEQ ID NO 2
<211> LENGTH: 8
<212> TYPE: PRT
<213> ORGANISM: Artificial sequence
```

```
<220> FEATURE:
<223> OTHER INFORMATION: A peptide sequence derived from Amyloid beta
      (16-23)

<400> SEQUENCE: 2

Lys Leu Val Phe Phe Ala Glu Asp
1               5

<210> SEQ ID NO 3
<211> LENGTH: 11
<212> TYPE: PRT
<213> ORGANISM: Artificial sequence
<220> FEATURE:
<223> OTHER INFORMATION: A peptide sequence derived from Amylin (45-55)

<400> SEQUENCE: 3

Leu Ala Asn Phe Leu Val His Ser Ser Asn Asn
1               5                   10

<210> SEQ ID NO 4
<211> LENGTH: 7
<212> TYPE: PRT
<213> ORGANISM: Artificial sequence
<220> FEATURE:
<223> OTHER INFORMATION: A peptide sequence derived from Glucagon
      (74-80)

<400> SEQUENCE: 4

Phe Val Gln Trp Leu Met Asn
1               5

<210> SEQ ID NO 5
<211> LENGTH: 27
<212> TYPE: PRT
<213> ORGANISM: Artificial sequence
<220> FEATURE:
<223> OTHER INFORMATION: A peptide sequence derived from VZV gE (24-50)

<400> SEQUENCE: 5

Ile Thr Asn Pro Val Arg Ala Ser Val Leu Arg Tyr Asp Asp Phe His
1               5                   10                  15

Thr Asp Glu Asp Lys Leu Asp Thr Asn Ser Val
            20                  25

<210> SEQ ID NO 6
<211> LENGTH: 4
<212> TYPE: PRT
<213> ORGANISM: Artificial sequence
<220> FEATURE:
<223> OTHER INFORMATION: A peptide sequence derived from Insulin B chain
      (25-28) N'

<400> SEQUENCE: 6

Phe Val Asn Gln
1

<210> SEQ ID NO 7
<211> LENGTH: 4
<212> TYPE: PRT
<213> ORGANISM: Artificial sequence
<220> FEATURE:
<223> OTHER INFORMATION: A peptide sequence derived from Amylin (34-37)
      N'

<400> SEQUENCE: 7

Lys Cys Asn Thr
1
```

-continued

```
<210> SEQ ID NO 8
<211> LENGTH: 4
<212> TYPE: PRT
<213> ORGANISM: Artificial sequence
<220> FEATURE:
<223> OTHER INFORMATION: A peptide sequence derived from Glucagon
      (53-56) N'

<400> SEQUENCE: 8

His Ser Gln Gly
1

<210> SEQ ID NO 9
<211> LENGTH: 8
<212> TYPE: PRT
<213> ORGANISM: Artificial sequence
<220> FEATURE:
<223> OTHER INFORMATION: A peptide sequence derived from VZV gE (24-31)
      N'

<400> SEQUENCE: 9

Ile Thr Asn Pro Val Arg Ala Ser
1               5

<210> SEQ ID NO 10
<211> LENGTH: 4
<212> TYPE: PRT
<213> ORGANISM: Artificial sequence
<220> FEATURE:
<223> OTHER INFORMATION: Amyloid beta (1-4) deived peptide

<400> SEQUENCE: 10

Asp Ala Glu Phe
1

<210> SEQ ID NO 11
<211> LENGTH: 9
<212> TYPE: PRT
<213> ORGANISM: Artificial sequence
<220> FEATURE:
<223> OTHER INFORMATION: Insulysin (IDE) FRET substrate
<220> FEATURE:
<221> NAME/KEY: misc_feature
<223> OTHER INFORMATION: N' Mca conjugated peptide
<220> FEATURE:
<221> NAME/KEY: misc_feature
<223> OTHER INFORMATION: C' EDDnp conjugated peptide

<400> SEQUENCE: 11

Gly Gly Phe Leu Arg Lys His Gly Gln
1               5

<210> SEQ ID NO 12
<211> LENGTH: 48
<212> TYPE: PRT
<213> ORGANISM: Artificial sequence
<220> FEATURE:
<223> OTHER INFORMATION: VZV gE derived amino acid residues 24-71

<400> SEQUENCE: 12

Ile Thr Asn Pro Val Arg Ala Ser Val Leu Arg Tyr Asp Asp Phe His
1               5                   10                  15

Thr Asp Glu Asp Lys Leu Asp Thr Asn Ser Val Tyr Glu Pro Tyr Tyr
            20                  25                  30

His Ser Asp His Ala Glu Ser Ser Trp Val Asn Arg Gly Glu Ser Ser
        35                  40                  45
```

```
<210> SEQ ID NO 13
<211> LENGTH: 6
<212> TYPE: PRT
<213> ORGANISM: Artificial sequence
<220> FEATURE:
<223> OTHER INFORMATION: A flexible peptide moiety

<400> SEQUENCE: 13

Gly Ser Gly Gly Ser Ser
1               5

<210> SEQ ID NO 14
<211> LENGTH: 10
<212> TYPE: PRT
<213> ORGANISM: Artificial sequence
<220> FEATURE:
<223> OTHER INFORMATION: ADT-1 IDE inhibitory peptide

<400> SEQUENCE: 14

Val Leu Arg Tyr Asp Asp Phe His Thr Asp
1               5                   10

<210> SEQ ID NO 15
<211> LENGTH: 10
<212> TYPE: PRT
<213> ORGANISM: Artificial sequence
<220> FEATURE:
<223> OTHER INFORMATION: ADT-2 IDE inhibitory peptide

<400> SEQUENCE: 15

Glu Ala Leu Tyr Asp Asp Leu Val Cys Gly
1               5                   10

<210> SEQ ID NO 16
<211> LENGTH: 13
<212> TYPE: PRT
<213> ORGANISM: Artificial sequence
<220> FEATURE:
<223> OTHER INFORMATION: ADT-3 IDE inhibitory peptide

<400> SEQUENCE: 16

Leu Ala Asn Phe Asp Asp Leu Val His Ser Ser Asn Asn
1               5                   10

<210> SEQ ID NO 17
<211> LENGTH: 9
<212> TYPE: PRT
<213> ORGANISM: Artificial sequence
<220> FEATURE:
<223> OTHER INFORMATION: ADT-4 IDE inhibitory peptide

<400> SEQUENCE: 17

Phe Val Gln Trp Asp Asp Leu Met Asn
1               5

<210> SEQ ID NO 18
<211> LENGTH: 10
<212> TYPE: PRT
<213> ORGANISM: Artificial sequence
<220> FEATURE:
<223> OTHER INFORMATION: ADT-5 IDE inhibitory peptide

<400> SEQUENCE: 18

Lys Leu Val Phe Asp Asp Phe Ala Glu Asp
1               5                   10

<210> SEQ ID NO 19
<211> LENGTH: 20
```

```
<212> TYPE: PRT
<213> ORGANISM: Artificial sequence
<220> FEATURE:
<223> OTHER INFORMATION: ADT-21 IDE inhibitory peptide

<400> SEQUENCE: 19

Ile Thr Asn Pro Gly Ser Gly Gly Ser Ser Val Leu Arg Tyr Asp Asp
1               5                   10                  15

Phe His Thr Asp
            20

<210> SEQ ID NO 20
<211> LENGTH: 20
<212> TYPE: PRT
<213> ORGANISM: Artificial sequence
<220> FEATURE:
<223> OTHER INFORMATION: ADT-22 IDE inhibitory peptide

<400> SEQUENCE: 20

Phe Val Asn Gln Gly Ser Gly Gly Ser Ser Glu Ala Leu Tyr Asp Asp
1               5                   10                  15

Leu Val Cys Gly
            20

<210> SEQ ID NO 21
<211> LENGTH: 23
<212> TYPE: PRT
<213> ORGANISM: Artificial sequence
<220> FEATURE:
<223> OTHER INFORMATION: ADT-23 IDE inhibitory peptide

<400> SEQUENCE: 21

Lys Cys Asn Thr Gly Ser Gly Gly Ser Ser Leu Ala Asn Phe Asp Asp
1               5                   10                  15

Leu Val His Ser Ser Asn Asn
            20

<210> SEQ ID NO 22
<211> LENGTH: 19
<212> TYPE: PRT
<213> ORGANISM: Artificial sequence
<220> FEATURE:
<223> OTHER INFORMATION: ADT-24 IDE inhibitory peptide

<400> SEQUENCE: 22

His Ser Gln Gly Gly Ser Gly Gly Ser Ser Phe Val Gln Trp Asp Asp
1               5                   10                  15

Leu Met Asn

<210> SEQ ID NO 23
<211> LENGTH: 20
<212> TYPE: PRT
<213> ORGANISM: Artificial sequence
<220> FEATURE:
<223> OTHER INFORMATION: ADT-25 IDE inhibitory peptide

<400> SEQUENCE: 23

Asp Ala Glu Phe Gly Ser Gly Gly Ser Ser Lys Leu Val Phe Asp Asp
1               5                   10                  15

Phe Ala Glu Asp
            20

<210> SEQ ID NO 24
<211> LENGTH: 4
<212> TYPE: PRT
```

```
<213> ORGANISM: Artificial sequence
<220> FEATURE:
<223> OTHER INFORMATION: VZV N' derived peptide sequence

<400> SEQUENCE: 24

Ile Thr Asn Pro
1

<210> SEQ ID NO 25
<211> LENGTH: 4
<212> TYPE: PRT
<213> ORGANISM: Artificial sequence
<220> FEATURE:
<223> OTHER INFORMATION: Amyliod beta N' derived peptide sequence

<400> SEQUENCE: 25

Asp Ala Glu Phe
1

<210> SEQ ID NO 26
<211> LENGTH: 2
<212> TYPE: PRT
<213> ORGANISM: Artificial sequence
<220> FEATURE:
<223> OTHER INFORMATION: Examplary Insulin-Degrading Enzyme (IDE)
      inhibitory peptide.

<400> SEQUENCE: 26

Asp Asp
1

<210> SEQ ID NO 27
<211> LENGTH: 30
<212> TYPE: DNA
<213> ORGANISM: Artificial sequence
<220> FEATURE:
<223> OTHER INFORMATION: ADT-1 polynucleotide sequence

<400> SEQUENCE: 27
gtgctgcgct atgatgattt tcataccgat                                      30

<210> SEQ ID NO 28
<211> LENGTH: 30
<212> TYPE: DNA
<213> ORGANISM: Artificial sequence
<220> FEATURE:
<223> OTHER INFORMATION: ADT-2 polynucleotide sequence

<400> SEQUENCE: 28
gaagcgctgt atgatgatct ggtgtgcggc                                      30

<210> SEQ ID NO 29
<211> LENGTH: 39
<212> TYPE: DNA
<213> ORGANISM: Artificial sequence
<220> FEATURE:
<223> OTHER INFORMATION: ADT-3 polynucleotide sequence

<400> SEQUENCE: 29
ctggcgaact tgatgatct ggtgcatagc agcaacaac                             39

<210> SEQ ID NO 30
<211> LENGTH: 27
<212> TYPE: DNA
<213> ORGANISM: Artificial sequence
<220> FEATURE:
<223> OTHER INFORMATION: ADT-4 polynucleotide sequence
```

```
<400> SEQUENCE: 30
tttgtgcagt gggatgatct gatgaac                                27

<210> SEQ ID NO 31
<211> LENGTH: 30
<212> TYPE: DNA
<213> ORGANISM: Artificial sequence
<220> FEATURE:
<223> OTHER INFORMATION: ADT-5 polynucleotide sequence

<400> SEQUENCE: 31
aaactggtgt ttgatgattt tgcggaagat                             30

<210> SEQ ID NO 32
<211> LENGTH: 60
<212> TYPE: DNA
<213> ORGANISM: Artificial sequence
<220> FEATURE:
<223> OTHER INFORMATION: ADT-21 polynucleotide sequence

<400> SEQUENCE: 32
attaccaacc cgggcagcgg cggcagcagc gtgctgcgct atgatgattt tcataccgat    60

<210> SEQ ID NO 33
<211> LENGTH: 60
<212> TYPE: DNA
<213> ORGANISM: Artificial sequence
<220> FEATURE:
<223> OTHER INFORMATION: ADT-22 polynucleotide sequence

<400> SEQUENCE: 33
tttgtgaacc agggcagcgg cggcagcagc gaagcgctgt atgatgatct ggtgtgcggc    60

<210> SEQ ID NO 34
<211> LENGTH: 69
<212> TYPE: DNA
<213> ORGANISM: Artificial sequence
<220> FEATURE:
<223> OTHER INFORMATION: ADT-23 polynucleotide sequence

<400> SEQUENCE: 34
aaatgcaaca ccggcagcgg cggcagcagc ctggcgaact tgatgatct ggtgcatagc    60 agcaacaac                                                    69

<210> SEQ ID NO 35
<211> LENGTH: 57
<212> TYPE: DNA
<213> ORGANISM: Artificial sequence
<220> FEATURE:
<223> OTHER INFORMATION: ADT-24 polynucleotide sequence

<400> SEQUENCE: 35
catagccagg gcggcagcgg cggcagcagc tttgtgcagt gggatgatct gatgaac       57

<210> SEQ ID NO 36
<211> LENGTH: 60
<212> TYPE: DNA
<213> ORGANISM: Artificial sequence
<220> FEATURE:
<223> OTHER INFORMATION: ADT-25 polynucleotide sequence

<400> SEQUENCE: 36
gatgcggaat tggcagcgg cggcagcagc aaactggtgt ttgatgattt tgcggaagat    60

<210> SEQ ID NO 37
```

```
<211> LENGTH: 6
<212> TYPE: DNA
<213> ORGANISM: Artificial sequence
<220> FEATURE:
<223> OTHER INFORMATION: ADT-31 polynucleotide sequence

<400> SEQUENCE: 37 gatgat                                                                    6

<210> SEQ ID NO 38
<211> LENGTH: 30
<212> TYPE: DNA
<213> ORGANISM: Artificial sequence
<220> FEATURE:
<223> OTHER INFORMATION: ADT-32 polynucleotide sequence

<400> SEQUENCE: 38
gatgatgaag cgctgtatct ggtgtgcggc                                         30

<210> SEQ ID NO 39
<211> LENGTH: 30
<212> TYPE: DNA
<213> ORGANISM: Artificial sequence
<220> FEATURE:
<223> OTHER INFORMATION: ADT-33 polynucleotide sequence

<400> SEQUENCE: 39
gaagcgctgt ataacaacct ggtgtgcggc                                         30

<210> SEQ ID NO 40
<211> LENGTH: 30
<212> TYPE: DNA
<213> ORGANISM: Artificial sequence
<220> FEATURE:
<223> OTHER INFORMATION: ADT-34 polynucleotide sequence

<400> SEQUENCE: 40
gaagcgctgt atgcggcgct ggtgtgcggc                                         30

<210> SEQ ID NO 41
<211> LENGTH: 30
<212> TYPE: DNA
<213> ORGANISM: Artificial sequence
<220> FEATURE:
<223> OTHER INFORMATION: ADT-35 polynucleotide sequence

<400> SEQUENCE: 41
gaagcgctgt atttttttct ggtgtgcggc                                         30

<210> SEQ ID NO 42
<211> LENGTH: 60
<212> TYPE: DNA
<213> ORGANISM: Artificial sequence
<220> FEATURE:
<223> OTHER INFORMATION: ADT-41 polynucleotide sequence

<400> SEQUENCE: 42
attaccaacc cgggcagcgg cggcagcagc gaagcgctgt atgatgatct ggtgtgcggc        60

<210> SEQ ID NO 43
<211> LENGTH: 69
<212> TYPE: DNA
<213> ORGANISM: Artificial sequence
<220> FEATURE:
<223> OTHER INFORMATION: ADT-42 polynucleotide sequence

<400> SEQUENCE: 43
```

-continued attaccaacc cgggcagcgg cggcagcagc ctggcgaact ttgatgatct ggtgcatagc    60
agcaacaac    69

<210> SEQ ID NO 44
<211> LENGTH: 57
<212> TYPE: DNA
<213> ORGANISM: Artificial sequence
<220> FEATURE:
<223> OTHER INFORMATION: ADT-43 polynucleotide sequence

<400> SEQUENCE: 44
attaccaacc cgggcagcgg cggcagcagc tttgtgcagt gggatgatct gatgaac    57

<210> SEQ ID NO 45
<211> LENGTH: 60
<212> TYPE: DNA
<213> ORGANISM: Artificial sequence
<220> FEATURE:
<223> OTHER INFORMATION: ADT-44 polynucleotide sequence

<400> SEQUENCE: 45
attaccaacc cgggcagcgg cggcagcagc aaactggtgt tgatgatttt tgcggaagat    60

<210> SEQ ID NO 46
<211> LENGTH: 60
<212> TYPE: DNA
<213> ORGANISM: Artificial sequence
<220> FEATURE:
<223> OTHER INFORMATION: ADT-51 polynucleotide sequence

<400> SEQUENCE: 46
tttgtgaacc agggcagcgg cggcagcagc gtgctgcgct atgatgattt tcataccgat    60

<210> SEQ ID NO 47
<211> LENGTH: 69
<212> TYPE: DNA
<213> ORGANISM: Artificial sequence
<220> FEATURE:
<223> OTHER INFORMATION: ADT-52 polynucleotide sequence

<400> SEQUENCE: 47
tttgtgaacc agggcagcgg cggcagcagc ctggcgaact ttgatgatct ggtgcatagc    60
agcaacaac    69

<210> SEQ ID NO 48
<211> LENGTH: 57
<212> TYPE: DNA
<213> ORGANISM: Artificial sequence
<220> FEATURE:
<223> OTHER INFORMATION: ADT-53 polynucleotide sequence

<400> SEQUENCE: 48
tttgtgaacc agggcagcgg cggcagcagc tttgtgcagt gggatgatct gatgaac    57

<210> SEQ ID NO 49
<211> LENGTH: 60
<212> TYPE: DNA
<213> ORGANISM: Artificial sequence
<220> FEATURE:
<223> OTHER INFORMATION: ADT-54 polynucleotide sequence

<400> SEQUENCE: 49
tttgtgaacc agggcagcgg cggcagcagc aaactggtgt tgatgatttt tgcggaagat    60

<210> SEQ ID NO 50

```
<211> LENGTH: 60
<212> TYPE: DNA
<213> ORGANISM: Artificial sequence
<220> FEATURE:
<223> OTHER INFORMATION: ADT-61 polynucleotide sequence

<400> SEQUENCE: 50
aaatgcaaca ccggcagcgg cggcagcagc gtgctgcgct atgatgattt tcataccgat    60

<210> SEQ ID NO 51
<211> LENGTH: 60
<212> TYPE: DNA
<213> ORGANISM: Artificial sequence
<220> FEATURE:
<223> OTHER INFORMATION: ADT-62 polynucleotide sequence

<400> SEQUENCE: 51
aaatgcaaca ccggcagcgg cggcagcagc gaagcgctgt atgatgatct ggtgtgcggc    60

<210> SEQ ID NO 52
<211> LENGTH: 57
<212> TYPE: DNA
<213> ORGANISM: Artificial sequence
<220> FEATURE:
<223> OTHER INFORMATION: ADT-63 polynucleotide sequence

<400> SEQUENCE: 52
aaatgcaaca ccggcagcgg cggcagcagc tttgtgcagt gggatgatct gatgaac       57

<210> SEQ ID NO 53
<211> LENGTH: 60
<212> TYPE: DNA
<213> ORGANISM: Artificial sequence
<220> FEATURE:
<223> OTHER INFORMATION: ADT-64 polynucleotide sequence

<400> SEQUENCE: 53
aaatgcaaca ccggcagcgg cggcagcagc aaactggtgt ttgatgattt tgcggaagat    60

<210> SEQ ID NO 54
<211> LENGTH: 60
<212> TYPE: DNA
<213> ORGANISM: Artificial sequence
<220> FEATURE:
<223> OTHER INFORMATION: ADT-71 polynucleotide sequence

<400> SEQUENCE: 54
catagccagg gcggcagcgg cggcagcagc gtgctgcgct atgatgattt tcataccgat    60

<210> SEQ ID NO 55
<211> LENGTH: 60
<212> TYPE: DNA
<213> ORGANISM: Artificial sequence
<220> FEATURE:
<223> OTHER INFORMATION: ADT-72 polynucleotide sequence

<400> SEQUENCE: 55
catagccagg gcggcagcgg cggcagcagc gaagcgctgt atgatgatct ggtgtgcggc    60

<210> SEQ ID NO 56
<211> LENGTH: 69
<212> TYPE: DNA
<213> ORGANISM: Artificial sequence
<220> FEATURE:
<223> OTHER INFORMATION: ADT-73 polynucleotide sequence

<400> SEQUENCE: 56
```

```
catagccagg gcggcagcgg cggcagcagc ctggcgaact ttgatgatct ggtgcatagc     60
agcaacaac                                                             69

<210> SEQ ID NO 57
<211> LENGTH: 60
<212> TYPE: DNA
<213> ORGANISM: Artificial sequence
<220> FEATURE:
<223> OTHER INFORMATION: ADT-74 polynucleotide sequence

<400> SEQUENCE: 57
catagccagg gcggcagcgg cggcagcagc aaactggtgt ttgatgattt tgcggaagat     60

<210> SEQ ID NO 58
<211> LENGTH: 60
<212> TYPE: DNA
<213> ORGANISM: Artificial sequence
<220> FEATURE:
<223> OTHER INFORMATION: ADT-81 polynucleotide sequence

<400> SEQUENCE: 58
gatgcggaat tggcagcgg cggcagcagc gtgctgcgct atgatgattt tcataccgat      60

<210> SEQ ID NO 59
<211> LENGTH: 60
<212> TYPE: DNA
<213> ORGANISM: Artificial sequence
<220> FEATURE:
<223> OTHER INFORMATION: ADT-82 polynucleotide sequence

<400> SEQUENCE: 59
gatgcggaat tggcagcgg cggcagcagc gaagcgctgt atgatgatct ggtgtgcggc      60

<210> SEQ ID NO 60
<211> LENGTH: 69
<212> TYPE: DNA
<213> ORGANISM: Artificial sequence
<220> FEATURE:
<223> OTHER INFORMATION: ADT-83 polynucleotide sequence

<400> SEQUENCE: 60
gatgcggaat tggcagcgg cggcagcagc ctggcgaact ttgatgatct ggtgcatagc      60
agcaacaac                                                             69

<210> SEQ ID NO 61
<211> LENGTH: 57
<212> TYPE: DNA
<213> ORGANISM: Artificial sequence
<220> FEATURE:
<223> OTHER INFORMATION: ADT-84 polynucleotide sequence

<400> SEQUENCE: 61
gatgcggaat tggcagcgg cggcagcagc tttgtgcagt gggatgatct gatgaac        57

<210> SEQ ID NO 62
<211> LENGTH: 10
<212> TYPE: PRT
<213> ORGANISM: Artificial sequence
<220> FEATURE:
<223> OTHER INFORMATION: ADT-32 IDE inhibitory peptide

<400> SEQUENCE: 62

Asp Asp Glu Ala Leu Tyr Leu Val Cys Gly
1               5                   10
```

<210> SEQ ID NO 63
<211> LENGTH: 10
<212> TYPE: PRT
<213> ORGANISM: Artificial sequence
<220> FEATURE:
<223> OTHER INFORMATION: ADT-33 IDE inhibitory peptide

<400> SEQUENCE: 63

Glu Ala Leu Tyr Asn Asn Leu Val Cys Gly
1               5                   10

<210> SEQ ID NO 64
<211> LENGTH: 10
<212> TYPE: PRT
<213> ORGANISM: Artificial sequence
<220> FEATURE:
<223> OTHER INFORMATION: ADT-34 IDE inhibitory peptide

<400> SEQUENCE: 64

Glu Ala Leu Tyr Ala Ala Leu Val Cys Gly
1               5                   10

<210> SEQ ID NO 65
<211> LENGTH: 10
<212> TYPE: PRT
<213> ORGANISM: Artificial sequence
<220> FEATURE:
<223> OTHER INFORMATION: ADT-35 IDE inhibitory peptide

<400> SEQUENCE: 65

Glu Ala Leu Tyr Phe Phe Leu Val Cys Gly
1               5                   10

<210> SEQ ID NO 66
<211> LENGTH: 10
<212> TYPE: PRT
<213> ORGANISM: Artificial sequence
<220> FEATURE:
<223> OTHER INFORMATION: ADT-36 IDE inhibitory peptide

<400> SEQUENCE: 66

Glu Ala Leu Tyr Glu Glu Leu Val Cys Gly
1               5                   10

<210> SEQ ID NO 67
<211> LENGTH: 20
<212> TYPE: PRT
<213> ORGANISM: Artificial sequence
<220> FEATURE:
<223> OTHER INFORMATION: ADT-41 IDE inhibitory peptide

<400> SEQUENCE: 67

Ile Thr Asn Pro Gly Ser Gly Gly Ser Ser Glu Ala Leu Tyr Asp Asp
1               5                   10                  15

Leu Val Cys Gly
            20

<210> SEQ ID NO 68
<211> LENGTH: 23
<212> TYPE: PRT
<213> ORGANISM: Artificial sequence
<220> FEATURE:
<223> OTHER INFORMATION: ADT-42 IDE inhibitory peptide

<400> SEQUENCE: 68

Ile Thr Asn Pro Gly Ser Gly Gly Ser Ser Leu Ala Asn Phe Asp Asp
1               5                   10                  15

```
Leu Val His Ser Ser Asn Asn
            20

<210> SEQ ID NO 69
<211> LENGTH: 19
<212> TYPE: PRT
<213> ORGANISM: Artificial sequence
<220> FEATURE:
<223> OTHER INFORMATION: ADT-43 IDE inhibitory peptide

<400> SEQUENCE: 69

Ile Thr Asn Pro Gly Ser Gly Gly Ser Ser Phe Val Gln Trp Asp Asp
1               5                   10                  15

Leu Met Asn

<210> SEQ ID NO 70
<211> LENGTH: 20
<212> TYPE: PRT
<213> ORGANISM: Artificial sequence
<220> FEATURE:
<223> OTHER INFORMATION: ADT-44 IDE inhibitory peptide

<400> SEQUENCE: 70

Ile Thr Asn Pro Gly Ser Gly Gly Ser Ser Lys Leu Val Phe Asp Asp
1               5                   10                  15

Phe Ala Glu Asp
            20

<210> SEQ ID NO 71
<211> LENGTH: 20
<212> TYPE: PRT
<213> ORGANISM: Artificial sequence
<220> FEATURE:
<223> OTHER INFORMATION: ADT-51 IDE inhibitory peptide

<400> SEQUENCE: 71

Phe Val Asn Gln Gly Ser Gly Gly Ser Ser Val Leu Arg Tyr Asp Asp
1               5                   10                  15

Phe His Thr Asp
            20

<210> SEQ ID NO 72
<211> LENGTH: 23
<212> TYPE: PRT
<213> ORGANISM: Artificial sequence
<220> FEATURE:
<223> OTHER INFORMATION: ADT-52 IDE inhibitory peptide

<400> SEQUENCE: 72

Phe Val Asn Gln Gly Ser Gly Gly Ser Ser Leu Ala Asn Phe Asp Asp
1               5                   10                  15

Leu Val His Ser Ser Asn Asn
            20

<210> SEQ ID NO 73
<211> LENGTH: 19
<212> TYPE: PRT
<213> ORGANISM: Artificial sequence
<220> FEATURE:
<223> OTHER INFORMATION: ADT-53 IDE inhibitory peptide

<400> SEQUENCE: 73

Phe Val Asn Gln Gly Ser Gly Gly Ser Ser Phe Val Gln Trp Asp Asp
1               5                   10                  15

Leu Met Asn
```

```
<210> SEQ ID NO 74
<211> LENGTH: 20
<212> TYPE: PRT
<213> ORGANISM: Artificial sequence
<220> FEATURE:
<223> OTHER INFORMATION: ADT-54 IDE inhibitory peptide

<400> SEQUENCE: 74

Phe Val Asn Gln Gly Ser Gly Gly Ser Ser Lys Leu Val Phe Asp Asp
1               5                   10                  15

Phe Ala Glu Asp
            20

<210> SEQ ID NO 75
<211> LENGTH: 20
<212> TYPE: PRT
<213> ORGANISM: Artificial sequence
<220> FEATURE:
<223> OTHER INFORMATION: ADT-61 IDE inhibitory peptide

<400> SEQUENCE: 75

Lys Cys Asn Thr Gly Ser Gly Gly Ser Ser Val Leu Arg Tyr Asp Asp
1               5                   10                  15

Phe His Thr Asp
            20

<210> SEQ ID NO 76
<211> LENGTH: 20
<212> TYPE: PRT
<213> ORGANISM: Artificial sequence
<220> FEATURE:
<223> OTHER INFORMATION: ADT-62 IDE inhibitory peptide

<400> SEQUENCE: 76

Lys Cys Asn Thr Gly Ser Gly Gly Ser Ser Glu Ala Leu Tyr Asp Asp
1               5                   10                  15

Leu Val Cys Gly
            20

<210> SEQ ID NO 77
<211> LENGTH: 19
<212> TYPE: PRT
<213> ORGANISM: Artificial sequence
<220> FEATURE:
<223> OTHER INFORMATION: ADT-63 IDE inhibitory peptide

<400> SEQUENCE: 77

Lys Cys Asn Thr Gly Ser Gly Gly Ser Ser Phe Val Gln Trp Asp Asp
1               5                   10                  15

Leu Met Asn

<210> SEQ ID NO 78
<211> LENGTH: 20
<212> TYPE: PRT
<213> ORGANISM: Artificial sequence
<220> FEATURE:
<223> OTHER INFORMATION: ADT-64 IDE inhibitory peptide

<400> SEQUENCE: 78

Lys Cys Asn Thr Gly Ser Gly Gly Ser Ser Lys Leu Val Phe Asp Asp
1               5                   10                  15

Phe Ala Glu Asp
            20
```

```
<210> SEQ ID NO 79
<211> LENGTH: 20
<212> TYPE: PRT
<213> ORGANISM: Artificial sequence
<220> FEATURE:
<223> OTHER INFORMATION: ADT-71 IDE inhibitory peptide

<400> SEQUENCE: 79

His Ser Gln Gly Gly Ser Gly Gly Ser Ser Val Leu Arg Tyr Asp Asp
1               5                   10                  15

Phe His Thr Asp
            20

<210> SEQ ID NO 80
<211> LENGTH: 20
<212> TYPE: PRT
<213> ORGANISM: Artificial sequence
<220> FEATURE:
<223> OTHER INFORMATION: ADT-72 IDE inhibitory peptide

<400> SEQUENCE: 80

His Ser Gln Gly Gly Ser Gly Gly Ser Ser Glu Ala Leu Tyr Asp Asp
1               5                   10                  15

Leu Val Cys Gly
            20

<210> SEQ ID NO 81
<211> LENGTH: 23
<212> TYPE: PRT
<213> ORGANISM: Artificial sequence
<220> FEATURE:
<223> OTHER INFORMATION: ADT-73 IDE inhibitory peptide

<400> SEQUENCE: 81

His Ser Gln Gly Gly Ser Gly Gly Ser Ser Leu Ala Asn Phe Asp Asp
1               5                   10                  15

Leu Val His Ser Ser Asn Asn
            20

<210> SEQ ID NO 82
<211> LENGTH: 20
<212> TYPE: PRT
<213> ORGANISM: Artificial sequence
<220> FEATURE:
<223> OTHER INFORMATION: ADT-74 IDE inhibitory peptide

<400> SEQUENCE: 82

His Ser Gln Gly Gly Ser Gly Gly Ser Ser Lys Leu Val Phe Asp Asp
1               5                   10                  15

Phe Ala Glu Asp
            20

<210> SEQ ID NO 83
<211> LENGTH: 20
<212> TYPE: PRT
<213> ORGANISM: Artificial sequence
<220> FEATURE:
<223> OTHER INFORMATION: ADT-81 IDE inhibitory peptide

<400> SEQUENCE: 83

Asp Ala Glu Phe Gly Ser Gly Gly Ser Ser Val Leu Arg Tyr Asp Asp
1               5                   10                  15

Phe His Thr Asp
            20
```

```
<210> SEQ ID NO 84
<211> LENGTH: 20
<212> TYPE: PRT
<213> ORGANISM: Artificial sequence
<220> FEATURE:
<223> OTHER INFORMATION: ADT-82 IDE inhibitory peptide

<400> SEQUENCE: 84

Asp Ala Glu Phe Gly Ser Gly Gly Ser Ser Glu Ala Leu Tyr Asp Asp
1               5                   10                  15

Leu Val Cys Gly
            20

<210> SEQ ID NO 85
<211> LENGTH: 23
<212> TYPE: PRT
<213> ORGANISM: Artificial sequence
<220> FEATURE:
<223> OTHER INFORMATION: ADT-83 IDE inhibitory peptide

<400> SEQUENCE: 85

Asp Ala Glu Phe Gly Ser Gly Gly Ser Ser Leu Ala Asn Phe Asp Asp
1               5                   10                  15

Leu Val His Ser Ser Asn Asn
            20

<210> SEQ ID NO 86
<211> LENGTH: 19
<212> TYPE: PRT
<213> ORGANISM: Artificial sequence
<220> FEATURE:
<223> OTHER INFORMATION: ADT-84 IDE inhibitory peptide

<400> SEQUENCE: 86

Asp Ala Glu Phe Gly Ser Gly Gly Ser Ser Phe Val Gln Trp Asp Asp
1               5                   10                  15

Leu Met Asn

<210> SEQ ID NO 87
<211> LENGTH: 10
<212> TYPE: PRT
<213> ORGANISM: Artificial sequence
<220> FEATURE:
<223> OTHER INFORMATION: ADT5N IDE inhibitory peptide

<400> SEQUENCE: 87

Val Leu Arg Tyr Asn Asn Phe His Thr Asp
1               5                   10

<210> SEQ ID NO 88
<211> LENGTH: 18
<212> TYPE: PRT
<213> ORGANISM: Artificial sequence
<220> FEATURE:
<223> OTHER INFORMATION: VZV IDE inhibitory peptide

<400> SEQUENCE: 88

Ile Thr Asn Pro Val Arg Ala Ser Val Leu Arg Tyr Asp Asp Phe His
1               5                   10                  15

Thr Asp
```

PEPTIDES, PHARMACEUTICAL COMPOSITIONS COMPRISING SAME AND USES THEREOF

RELATED APPLICATIONS

This application is a National Phase of PCT patent application No. PCT/IL2010/000093 having International filing date of Feb. 2, 2010, which claims the benefit of priority of U.S. Provisional Patent Application No. 61/202,162 filed on Feb. 2, 2009. The contents of the above applications are all incorporated herein by reference.

FIELD AND BACKGROUND OF THE INVENTION

The present invention, in some embodiments thereof, relates to peptides and, more particularly, but not exclusively, to uses thereof in inhibiting Insulin-Degrading Enzymes (IDE).

Diabetes is a syndrome characterized by disordered metabolism and abnormally high blood sugar (hyperglycemia) resulting from insufficient levels of the hormone insulin. The most common forms of diabetes are Diabetes mellitus type 1, Diabetes mellitus type 2 and gestational diabetes. Diabetes is usually associated with excessive urine production, resulting compensatory thirst and increased fluid intake, blurred vision, unexplained weight loss, lethargy and changes in energy metabolism.

All types of diabetes have been treatable since insulin became medically available in 1921. Patients with Diabetes mellitus type 1 depend on external insulin (most commonly injected subcutaneously) as the hormone is no longer produced by their pancreas (by the islets of Langerhans). Patients with Diabetes mellitus type 2 or gestational diabetes are typically insulin resistant and may require insulin to control blood glucose levels [Vinik et al. (2004) MedGenMed 6:12].

In normal individuals (i.e. non-diabetics) increased insulin levels lead to glucose absorption and storage in cells, consequently reducing glycogen to glucose conversion, reducing blood glucose levels, and thereby reducing insulin release. Therefore, normally the blood glucose level rises somewhat after eating and within an hour or so returns to the normal 'fasting' level. When treating a patient with insulin (e.g. synthetic human insulin or insulin analogs) the right dose and the right timing of administration must be determined and achieving physiological regulation of blood glucose, as in non-diabetics, is attempted. However, treatment of diabetic patients with insulin usually falls far short of normal glucose control and maintaining the basal rate and the bolus rate is a continuous balancing act that patients with insulin-dependent diabetes must manage on a daily basis [Vinik et al., supra]. Moreover, there is often a reluctance on the part of many care providers to prescribe insulin due to fear of weight gain, hypoglycemia, cardiovascular consequences or because the patient is unwilling to co-operate. Furthermore, continuous injection of insulin increases the risk of insulin binding to antibodies that appear to be a strong risk factor for inexplicable severe hypoglycemia in patients with Diabetes mellitus type 1.

Insulin is critical for glucose, lipid, and protein metabolism as well as for cell growth and differentiation. It is cleared from the body mainly by the liver and kidney, but most other tissues also degrade insulin. Insulin-degrading enzyme (IDE, insulysin) is the major enzyme responsible for insulin degradation [Simkin et al. (1949) Arch Biochem 24:422-428]. IDE is an approximately 110 kDa thiol zinc-metalloendopeptidase located in cytosol, peroxisomes, endosomes, and on the cell surface. This enzyme cleaves small proteins of diverse sequences many of which share a propensity to form β-pleated sheet-rich amyloid fibrils, including amyloid β-protein (Aβ), insulin, glucagon, amylin, atrial natriuretic factor and calcitonin [Simkin et al., supra].

The IDE region of chromosome 10q has been genetically linked to type 2 diabetes mellitus [DM2, Ghosh et al. (2000) Am J Hum Genet 67:1174-1185; Wiltshire et al. (2002) Am J Hum Genet 70:543-546] and to elevated fasting glucose levels [Meigs et al. (2002) Diabetes 51:833-840]. Moreover, IDE$^{-/-}$ mice had hyperinsulinemia and glucose intolerance, hallmarks of DM2 [Farris et al. (2003) Proc Natl Acad Sci USA 100:4162-4167]. This model demonstrated that in vivo deficiency of a protease responsible for degrading insulin results in hyperglycemia in response to a glucose load (i.e., glucose intolerance).

Reports have further suggested the role of IDE in degradation of Aβ in Alzheimer's disease [Farris et al., supra]. The elevation of cerebral Aβ in IDE$^{-/-}$ model animals (approximately 10-65%) validated a role for IDE in Aβ proteolysis in vivo, however, there are most likely additional mechanisms of Aβ clearance in the intact brain, especially for Aβ42. Other proteases (e.g., NEP, endothelin-converting enzyme) may participate in Aβ clearance and partially compensate for the lack of IDE function.

IDE is also the cellular receptor mediating varicella-zoster virus (VZV) infection and cell-to-cell spreading [Li et al. (2006) Cell 127:305-316]. Down regulation of IDE by siRNA, or blocking IDE with an antibody, with a soluble IDE protein (extracted from the liver) or with a bacitracin inhibited VZV infection [Li et al., supra]. IDE interacts with glycoprotein E (gE), which is essential for virus infection, through the glycoprotein's extracellular domain, however, IDE does not degrade VZV.

The solved crystal structure of IDE [Shen et al. (2006) Nature 443:870-874] revealed that the amino- and carboxy-terminal domains of IDE (IDE-N and IDE-C, respectively) form a proteolytic chamber containing the zinc-binding active site, just large enough to encapsulate insulin. Extensive contacts between IDE-N and IDE-C keep the degradation chamber of IDE inaccessible to substrates. Repositioning of the IDE domains (shifting IDE-close to its active form IDE-open) enables substrate access to the catalytic cavity (FIG. 1). The activity of IDE toward a vast array of physiological substrates can be partially explained by the detailed crystal structure of the enzyme. The structural data revealed that IDE is shaped like a clam shell, consisting of two bowl-shaped halves connected by a flexible hinge, which allows the enzyme to exist in two conformations, closed and open. During catalytic processing of substrates, the enzyme switches from the open structure to the closed configuration and back to the open structure as IDE binds, catalyzes, and then releases its substrate, respectively. The extended hydrogen bonding between the two halves of IDE creates a "latch" that acts to maintain the enzyme in the closed state. Mutations that promote the open conformation have been shown to improve the protease's efficiency in cleaving the substrate by as much as 30- to 40-fold [Shen et al., supra]. As it was suggested that the rate-limiting step may be the speed at which the enzyme can reopen and then clamp down on a new morsel rather than the time it takes to chew something up.

U.S. Pat. Appl. No. 20030104981 discloses novel human insulin analogues for treating Diabetes Mellitus, the analogues being characterized by having enhanced stability to insulin-degrading enzyme (IDE) as well as achieving longer life times than native insulin. The insulin analogues taught by U.S. Pat. Appl. No. 20030104981 were characterized structurally by elimination of B26-B30 in the human insulin B-chain and by having at least one specified substitution at B10, B14 and B17.

U.S. Pat. No. 7,108,972 discloses polynucleotides and polypeptides and uses of same, including two NOV3 nucleic acid sequences encoding Insulysin-like proteins. According to U.S. Pat. No. 7,108,972, these Insulysin-like proteins may be used in diagnosis and therapeutics of various diseases and disorders including diabetes.

SUMMARY OF THE INVENTION

According to an aspect of some embodiments of the present invention there is provided a use of an isolated peptide comprising an amino acid sequence being no more than 25 amino acids in length, the amino acid sequence comprising at least one aspartate or a homolog thereof, the peptide having an Insulin-Degrading Enzyme (IDE) inhibitory activity, for the manufacture of a medicament identified for treating a disease selected from the group consisting of diabetes, obesity, hyperglycemia, retinal damage, renal failure, nerve damage, microvascular damage and varicella-zoster virus (VZV) infection.

According to an aspect of some embodiments of the present invention there is provided a use of an isolated peptide comprising an amino acid sequence being no more than 25 amino acids in length, the amino acid sequence comprising at least one aspartate or a homolog thereof, the peptide having an Insulin-Degrading Enzyme (IDE) inhibitory activity, for treating a disease selected from the group consisting of diabetes, obesity hyperglycemia, retinal damage, renal failure, nerve damage, microvascular damage and varicella-zoster virus (VZV) infection.

According to an aspect of some embodiments of the present invention there is provided a method of treating a disease selected from the group consisting of diabetes, obesity hyperglycemia, retinal damage, renal failure, nerve damage, microvascular damage and varicella-zoster virus (VZV) infection in a subject in need thereof, the method comprising administering to the subject an isolated peptide comprising an amino acid sequence being no more than 25 amino acids in length, the amino acid sequence comprising at least one aspartate or a homolog thereof, the peptide having an Insulin-Degrading Enzyme (IDE) inhibitory activity.

According to an aspect of some embodiments of the present invention there is provided an isolated peptide comprising an amino acid sequence being no more than 25 amino acids in length, the amino acid sequence comprising at least one aspartate or a homolog thereof, the peptide having an Insulin-Degrading Enzyme (IDE) inhibitory activity.

According to an aspect of some embodiments of the present invention there is provided a pharmaceutical composition comprising as an active ingredient the isolated peptide of any of claims 4-18 and a pharmaceutically acceptable carrier.

According to an aspect of some embodiments of the present invention there is provided an article of manufacture comprising the isolated peptide of any of claims 4-18 and insulin each being packaged in a packaging material and identified in print, in or on the packaging material for use in the treatment of diabetes.

According to an aspect of some embodiments of the present invention there is provided a method of identifying a peptide having an Insulin-degrading enzyme (IDE) inhibitory activity, the method comprising: contacting IDE with a reporter substrate of the IDE in a presence or absence of the peptide of any of claims 4-18, wherein a reduction in the reporter activity in the presence of the peptide is indicative of a peptide having the IDE inhibitory activity.

According to some embodiments of the invention, the amino acid sequence is selected from the group consisting of SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 26, SEQ ID NO: 62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO: 85 and SEQ ID NO:86.

According to some embodiments of the invention, the amino acid sequence is as set forth in SEQ ID NO: 19.

According to some embodiments of the invention, the amino acid sequence comprises a moiety which adds flexibility between the at least one aspartate or homolog thereof and an N-terminus sequence of the amino acid sequence.

According to some embodiments of the invention, the moiety which adds flexibility comprises an amino acid sequence.

According to some embodiments of the invention, the amino acid sequence comprises SEQ ID NO: 13.

According to some embodiments of the invention, the N-terminus sequence comprises an IDE binding sequence.

According to some embodiments of the invention, the amino acid sequence comprises an IDE binding sequence.

According to some embodiments of the invention, the IDE binding sequence is selected from the group consisting of SEQ ID NO: 6, SEQ ID NO: 7, SEQ ID NO: 8, SEQ ID NO: 24 and SEQ ID NO: 25.

According to some embodiments of the invention, the at least one aspartate or a homolog thereof comprises two aspartates or homologues thereof.

According to some embodiments of the invention, the two aspartates or homologues thereof are consecutively positioned in the peptide.

According to some embodiments of the invention, the homolog of the aspartate is a structural homologue.

According to some embodiments of the invention, the structural homologue comprises asparagine.

According to some embodiments of the invention, the homolog of the aspartate is a negatively charged amino acid.

According to some embodiments of the invention, the negatively charged amino acid is glutamic acid.

According to some embodiments of the invention, the administering is nasally administering.

According to some embodiments of the invention, the therapeutically effective amount results in an increase in blood insulin levels of the subject following the administering.

According to some embodiments of the invention, the therapeutically effective amount results in an increase in blood Insulin growth factor 1 (IGF1) levels of the subject following the administering.

According to some embodiments of the invention, the therapeutically effective amount results in reduction in secretion of IL-17 from T lymphocytes of the subject following the administering.

According to some embodiments of the invention, the therapeutically effective amount results in reduction in secretion of IFN-γ from T lymphocytes of the subject following the administering.

According to some embodiments of the invention, the therapeutically effective amount is between 0.1-10 µg per kg body weight.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
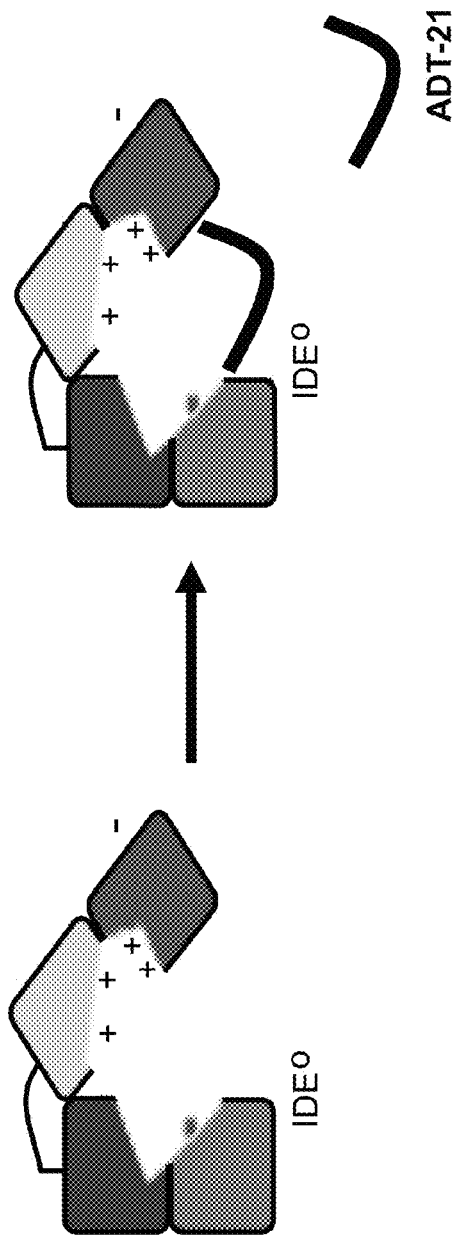

FIG. 1 depicts a model for inhibiting insulin-degrading enzymes (IDE) activity. The figure shows a model depicting IDE binding to an inhibitor of the present invention (for example ADT-21). The open state of IDE (IDE-open—IDE-°) allows substrate accession to the catalytic cavity, however, when the inhibitor binds the enzyme it inhibits the conformational change of IDE into its open state and keeps it in its closed state.

FIG. 2 depicts multiple sequence alignment (MSA) of the VZV IDE binding protein with other known substrates of IDE at the catalytic cleft binding segment. The MSA revealed similar features between the substrates and pointed out the VZV gE (24-50, SEQ ID NO: 5) amino acids as candidates that may contribute to IDE binding. Of note, the MSA also pointed out an important feature in the main cleavage site of VZV gE (DD repeats, SEQ ID NO: 26).

FIG. 3 depicts the design of short peptides with possible inhibition properties targeting the IDE Catalytic cleft.

FIG. 4 depicts the N-terminus binding segments of different IDE substrates. Of note, MSA revealed that Asn 3 is well reserved in Insulin B chain, Amylin and VZV gE.

FIG. 5 depicts the design of IDE inhibitors with co-effect: targeting the IDE N-terminus binding segment plus the Catalytic cleft. Of note, these IDE inhibitors also comprise a linker sequence.

FIG. 6 is a bar graph depicting a dose dependent inhibition of IDE activity by ADT-21 (SEQ ID NO: 19). In order to measure IDE activity, ELISA plates were coated with the target enzyme (IDE), plates were then incubated with the selected synthesized peptide candidate and enzymatic activity was measured compared to wells without the candidate peptide. IDE activity was measured using the InnoZyme™ Insulysin/IDE kit (IC50=100 nM), *p<0.0001; p<0.001. Of note, ADT-21 inhibits IDE activity in a dose dependant manner.

FIG. 7 depicts ADT21 inhibition of insulin degradation by IDE. Insulin (0.87 nM) isolated from bovine pancreas (SIGMA) was incubated with or without IDE (1.14 nM) along with ADT21 (SEQ ID NO: 19, 0.2 nM). Results represent three repeated experiments *p<0.05.

FIG. 8 depicts disease progression in NOD mice. The NOD mice model was used as a model for insulin dependent diabetes mellitus (IDDM). At 12 weeks of age mice were divided into 2 treatment groups (n=10-12). One group received, every other day, intranasal 10 μl ADT21 (3.76 μg/kg). The second group received PBS (control group). Mice were monitored for blood glucose levels using glucose test strips *p<0.05.

FIG. 9 depicts reduction in percent of diabetics in NOD mice following ADT21 treatment. 12 week old NOD mice [n=10-12] were treated with intranasal 10 μl ADT21 (treatment) or PBS (control) and were monitored weekly for blood glucose levels using glucose test strips. Onset of diabetes was marked by moderate glycosuria and by non-fasting plasma glucose higher than 250 mg/dl *p<0.05.

FIG. 10 depicts distribution of weight in NOD mice. 12 week old NOD mice were treated with 10 μl ADT21 (treatment) or PBS (control) and were monitored weekly for weight changes.

FIG. 11 depicts higher levels of blood insulin in ADT21 treated mice compared to control mice. NOD mice treated with 10 μl ADT21 were monitored for blood insulin levels at 30 weeks (using HTRF® Insulin assay) compared to non treated NOD mice (control) and non diabetic mice [n=6] *p<0.05, **p<0.01.

FIGS. 12A-C depict histological analysis of insulitis. At the age of 30 weeks, NOD mice treated or untreated with 10 μl ADT21 were sacrificed; their pancreata were isolated and stained with H&E staining. FIGS. 12A-B show sections of pancreas taken from control and ADT21-treated NOD mice. The figures illustrate pancreatic islets (magnification ×40); and FIG. 12C is a bar graph illustrating the insulitis scores (histological scores) of pancreas obtained from ADT21-treated and untreated mice (control) [n=6] *p=0.001.

FIG. 13 depicts higher IGF1 blood levels in ADT21-treated mice compared to control mice. NOD mice were monitored for blood levels of Insulin growth factor 1 (IGF1) at 30 week using AssayMax mouse IGF1 kit. [n=6] *p<0.05.

FIGS. 14A-B depict reduction in secretion of the pro-inflammatory cytokines IFN-γ and IL-17 from cells obtained from ADT21-treated mice. NOD mice (n=6-7), untreated or treated with 10 μl ADT21, at 30 weeks of age, were sacrificed and their splenocytes were isolated. The splenocytes were cultured at a concentration of $1\times10^{6}$ cells/well in 96-well plates and incubated with insulin 10 μg/ml. Supernatants were collect after 48 h of culture for cytokine measurements. Secretion of IFN-γ (FIG. 14A) or IL-17 (FIG. 14B) was measured by ELISA, *p<0.05.

FIGS. 15A-B depict reduction in secretion of the pro-inflammatory cytokines IFN-γ and IL-17 from CD4+ cells following co-culture with antigen presenting cells and ADT21. Following immunization of NOD mice with insulin, CD4+ T-cells were isolated from lymphoid tissue. The isolated CD4+ T-cells were then co-cultured with splenocytes isolated from non immunized NOD mice in the presence of insulin with or without ADT21. Secretion of IFN-γ (FIG. 15A) or IL-17 (FIG. 15B) was measured by ELISA [n=4], *p<0.05.

FIGS. 16A-B depict reduced pro-inflammatory cytokine production in IDE–/– mice. WT and IDE$^{-/-}$ mice were immunized with insulin. Spleens from these mice were isolated and the level of the immune response was measured. Secretion of IFN-γ (FIG. 16A) or IL-17 (FIG. 16B) was measured by ELISA [n=4], *p<0.05.

DESCRIPTION OF SPECIFIC EMBODIMENTS OF THE INVENTION

The present invention, in some embodiments thereof, relates to peptides and, more particularly, but not exclusively, to uses thereof in inhibiting Insulin-Degrading Enzymes (IDE).

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the present inventors have identified novel peptides which bind specifically to Insulin-Degrading Enzymes (IDE) (e.g., as set forth in GenBank Accession Nos. NM_004969 and NP_004960) and inhibit their enzymatic activity. These peptides may bind to the catalytic cleft of IDE but inhibit catalytic activity thereof and may thus be used as potent inhibitors of IDE and processing of it's natural substrates [e.g. insulin B chain and varicella-zoster virus (VZV)].

As is shown hereinbelow and in the Examples section which follows, the present inventors have unexpectedly identified, via multiple sequence alignments (MSA), a VZV glycoprotein E (gE) amino acid sequence (e.g., as set forth in GenBank Accession No. NP_040189) which is unique to VZV, binds specifically to the IDE catalytic cleft and which prevents enzymatic cleavage. This amino acid sequence comprises two repeats of the amino acid aspartate (D) (Asp13, Asp14, see FIG. 2). Furthermore, the present inventors have identified N-terminus binding segments (FIG. 4) of various IDE substrates. Taken together, identification of these sequences enabled generation of novel peptides which bind specifically to IDE and which may inhibit activation thereof (SEQ ID NOs: 14-18 and 19-23, FIGS. 3 and 5, respectively). To improve the conformational flexibility of the peptides and to enable increased binding to IDE, the present inventors have further added a moiety which adds flexibility (SEQ ID NO: 13) to the novel peptides of the present invention (FIG. 3). Additionally, the present inventors have shown that one of these novel peptides, ADT-21 (SEQ ID NO: 19) comprises specific IDE inhibitory properties (FIG. 6) and reduced insulin degradation (FIG. 7). ADT-21 was further shown to ameliorate Type 1 diabetes in Non-obese diabetic (NOD) mice when administered nasally (FIGS. 8-10) and to increase blood insulin levels (FIG. 11), thus allowing physiological regulation of blood glucose. Furthermore, ADT-21 was shown to increase IGF-1 levels in the serum of NOD mice (FIG. 13) and to reduce pro-inflammatory cytokine production in these mice (IFN-γ and IL-17 secretion, FIGS. 14A-B, respectively). Moreover, ADT21 was shown to reduce CD4+ T cell inflammatory response against insulin (FIGS. 15A-B).

Thus, according to one aspect of the present invention there is provided an isolated peptide comprising an amino acid sequence being no more than 25 amino acids in length, the amino acid sequence comprising at least one aspartate or a homolog thereof, the peptide having an Insulin-Degrading Enzyme (IDE) inhibitory activity.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, at least one modification (e.g., synthetic i.e., non-naturally occurring) rendering the peptides more stable while in a body or more capable of penetrating into cells. Such modifications are further described hereinbelow. The peptide is at least a di-peptide as will be further described hereinbelow.

As used herein the term "isolated" refers to a homogeneous preparation of the peptide which may be isolated from an environment where is naturally occurs.

According to an embodiment of the present invention, the peptide is no more than 2 amino acids in length, no more than 4 amino acids in length, no more than 6 amino acids in length, no more than 8 amino acids in length, no more than 10 amino acids in length, no more than 15 amino acids in length, no more than 20 amino acids in length or no more than 25 amino acids in length.

It will be appreciated that the peptide of the present invention comprises an Insulin-Degrading Enzyme (IDE) inhibitory activity.

As used herein, the term "Insulin-Degrading Enzyme (IDE)" refers to the insulysin or insulin protease, a large zinc-binding protease of the M16A metalloprotease subfamily which is involved in the cellular processing of multiple short polypeptides including insulin and glucagon (e.g., as set forth in GenBank Accession Nos. NM_004969 and NP_004960).

As used herein, the term "IDE inhibitory activity" refers to specifically down-regulating the enzymatic activity of IDE. For instance, the IC50 of IDE is in the range of 10-200 nM as assayed for ADT-21. According to exemplary embodiments, the peptide of the present invention is capable of down-regulating by at least 5%, at least 10%, at least 15%, at least 20%, at least 30%, at least 40%, at least 50%, at least 60%, at least 70%, at least 80%, at least 90% or at least 100% the enzymatic activity of IDE.

It will be appreciated that the IDE inhibitory activity of the peptide of the present invention results in reduction in secretion of IFN-γ and IL-17 from T lymphocytes (as depicted in Example 7). Furthermore, IDE inhibitory activity of the peptide of the present invention results in delayed progression of diabetes (as depicted in Example 4) and prevention of autoimmune response against insulin (Example 8).

It will be appreciated that IDE is a cellular enzyme which comprises an extracellular domain for substrate binding. Furthermore, IDE may also be secreted from the cells and thus, may bind its substrates extracellularly [Li et al. (2006) Cell 127:305-316; Shen et al. (2006) Nature 443:870-874]. Thus, it is envisioned by the present inventors that IDE will be inhibited by the peptides of the present invention by contacting on the cell surface or extracellularly.

As mentioned hereinabove, the peptide of the present invention comprises at least one aspartate or a homolog thereof.

As used herein, the term "aspartate or homolog thereof" refers to the amino acid aspartic acid or to an amino acid with a structural homology thereto. According to an exemplary embodiment, the structural homolog is aspargine. According to other exemplary embodiments the homolog is a negatively charged amino acid such as, but not limited to, glutamic acid.

According to an exemplary embodiment of the invention, the peptide may comprise one, two or more aspartates or homologues thereof. According to an exemplary embodiment, the peptide comprises two aspartates or homologues thereof.

According to one embodiment of this aspect of the present invention, the aspartates or homologous thereof are positioned consecutively in the peptide. An exemplary peptide of the present invention is as set forth in SEQ ID NO: 26.

It will be appreciated, that the aspartate or homolog thereof may be positioned anywhere within the peptide, such as within the N-terminus of the peptide, the C-terminus of the peptide or within the IDE catalytic cleft binding site of the peptide as to enable specific binding and inhibition of IDE by the peptide of the present invention. Thus, an exemplary amino acid sequence of the peptide of the present invention is as set forth in SEQ ID NO: 14, SEQ ID NO: 15, SEQ ID NO: 16, SEQ ID NO: 17, SEQ ID NO: 18, SEQ ID NO: 62, SEQ ID NO: 63, SEQ ID NO: 64, SEQ ID NO: 65 and SEQ ID NO: 66.

According to an embodiment of the present invention, the peptide may comprise an at least one IDE binding sequence (e.g., 1, 2, 3 or more) as for example set forth in SEQ ID NO: 6, SEQ ID NO: 7, SEQ ID NO: 8, SEQ ID NO: 24 or SEQ ID NO: 25. This sequence may be positioned anywhere in the peptide such as at the N-terminus of the peptide or C-terminus of the peptide.

It will be appreciated that the peptide of the present invention may further comprise a moiety which adds flexibility. Such a moiety may add flexibility to the peptide and allow conformational flexibility for increased binding and inhibition of IDE. A moiety which adds flexibility of the present teachings may include a peptide moiety or a chemical moiety, such as an organic polymer. It will be appreciated that the moiety which adds flexibility may comprise a covalent bond (e.g. a peptide bond) or a non-covalent bond.

Exemplary chemical crosslinking methods for moieties which add flexibility of the present invention are described herein below:

Thiol-amine Crosslinking:

In this scheme, an amine group of the peptide is indirectly conjugated to a thiol group, usually by a two- or three-step reaction sequence. The high reactivity of thiols and their relative rarity in most peptides make thiol groups ideal targets for controlled chemical crosslinking. Thiol groups may be introduced into the peptide using one of several thiolation methods including SPDP. The thiol-containing biomolecule is then reacted with an amine-containing biomolecule using a heterobifunctional crosslinking reagent.

Amine-amine Crosslinking:

Conjugation of the moiety element can be accomplished by methods known to those skilled in the art using amine-amine crosslinkers including, but not limited to glutaraldehyde, bis (imido esters), bis(succinimidyl esters), diisocyanates and diacid chlorides.

Carbodiimide Conjugation:

Conjugation of the moiety element can be accomplished by methods known to those skilled in the art using a dehydrating agent such as a carbodiimide. Most preferably the carbodiimide is used in the presence of 4-dimethyl aminopyridine. As is well known to those skilled in the art, carbodiimide conjugation can be used to form a covalent bond between a carboxyl group of one peptide and an hydroxyl group of a second peptide (resulting in the formation of an ester bond), or an amino group of a second peptide (resulting in the formation of an amide bond) or a sulfhydryl group of a second peptide (resulting in the formation of a thioester bond).

Likewise, carbodiimide coupling can be used to form analogous covalent bonds between a carbon group of a first peptide and an hydroxyl, amino or sulfhydryl group of a second peptide. See, generally, J. March, Advanced Organic Chemistry: Reaction's, Mechanism, and Structure, pp. 349-50 & 372-74 (3d ed.), 1985.

An exemplary moiety which adds flexibility of the present invention comprises an amino acid sequence, such as set forth in SEQ ID NO: 13.

It will be appreciated that the amino acid sequence of the moiety which adds flexibility may be positioned at any position within the peptide to allow conformational flexibility, as for example, between the aspartate or homolog thereof and the N-terminus sequence of the present invention (as depicted in FIG. 5).

Thus, according to another embodiment, the amino acid sequence of the peptide of the present invention is as set forth in SEQ ID NO: 19, SEQ ID NO: 20, SEQ ID NO: 21, SEQ ID NO: 22, SEQ ID NO: 23, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85 and SEQ ID NO: 86. According to an exemplary embodiment, the amino acid sequence is as set forth in SEQ ID NO: 19.

As mentioned, the peptides of the present invention may comprise modifications. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N (CH3)-CO—), ester bonds (—C(R)H—C—O—O—C(R)—N—), ketomethylene bonds (—CO—CH2-), α-aza bonds (—NH—N(R)—CO—), wherein R is any alkyl, e.g., methyl, carba bonds (—CH2-NH—), hydroxyethylene bonds (—CH (OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Conservative substitutions may be employed (e.g., as mentioned for the aspartate or homologs there of, above). Natural aromatic amino acids, Trp, Tyr and Phe, may be substituted for synthetic non-natural acid such as TIC, naphthylalanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodemosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
| --- | --- | --- | --- |
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-ethylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |

TABLE 2-continued

| Non-conventional amino acid | Code | Non-conventional amino acid | Code |
|---|---|---|---|
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α thylglutamine | Mgln | L-α-methylglutamate | Mglu |
| L-α-methylhistidine | Mhis | L-α-methylhomo phenylalanine | Mhphe |
| L-α-methylisoleucine | Mile | N-(2- methylthioethyl)glycine | Nmet |
| D-N-methylglutamine | Dnmgln | N-(3- guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α ethylhistidine | Mhis | L-α-methylhomophenylalanine | Mhphe |
| L-αthylisoleucine | Mile | N-(2- methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α ethylvaline | Mtrp | L-α-methyltyrosine | Mtyr |
| L-α-methylleucine | Mval Nnbhm | L-N- methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

The peptides of the present invention are preferably utilized in a linear form, although it will be appreciated that in cases where cyclization does not severely interfere with peptide characteristics, cyclic forms of the peptide can also be utilized.

It will be appreciated that since one of the main obstacles in using short peptide fragments in therapy is their proteolytic degradation by stereospecific cellular proteases, the peptides of the present invention preferably comprise at least one D-isomer of natural amino acids [i.e., inverso peptide analogues, Tjernberg (1997) J. Biol. Chem. 272:12601-5].

The peptides of the present invention may be synthesized by any techniques that are known to those skilled in the art of peptide synthesis, such as by using standard solid phase techniques. These methods include exclusive solid phase synthesis, partial solid phase synthesis methods, fragment condensation, classical solution synthesis. Solid phase peptide synthesis procedures are well known in the art and further described by John Morrow Stewart and Janis Dillaha Young, Solid Phase Polypeptide Syntheses (2nd Ed., Pierce Chemical Company, 1984).

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the peptide compounds of the present invention involves solid phase peptide synthesis.

Large scale peptide synthesis is described by Andersson Biopolymers 2000; 55(3):227-50.

Recombinant techniques may also be used to generate the peptides of the present invention. To produce a peptide of the present invention using recombinant technology, a nucleotide sequence (e.g. as set forth in SEQ ID NOs: 27-61, see Table 3 hereinbelow) encoding a peptide of the present invention is ligated into a nucleic acid expression vector, which comprises the nucleotide sequence under the transcriptional control of a cis-regulatory sequence (e.g., promoter sequence) suitable for directing constitutive, tissue specific or inducible transcription of the peptides of the present invention in the host cells.

TABLE 3

Exemplary nucleotide sequences of peptides of some embodiments of the present invention

| No. | Peptide | Sequence 5'-3' |
|---|---|---|
| 1 | ADT-1 | Gtgctgcgctatgatgattttcataccgat (SEQ ID NO: 27) |
| 2 | ADT-2 | Gaagcgctgtatgatgatctggtgtgcggc (SEQ ID NO: 28) |
| 3 | ADT-3 | Ctggcgaactttgatgatctggtgcatagcagcaacaac (SEQ ID NO: 29) |
| 4 | ADT-4 | Tttgtgcagtgggatgatctgatgaac (SEQ ID NO: 30) |
| 5 | ADT-5 | Aaactggtgtttgatgattttgcggaagat (SEQ ID NO: 31) |
| 6 | ADT-21 | Attaccaacccgggcagcggcggcagcagcgtgctgcgctatgatgattttcataccgat (SEQ ID NO: 32) |
| 7 | ADT-22 | Tttgtgaaccagggcagcggcggcagcagcgaagcgctgtatgatgatctggtgtgcggc (SEQ ID NO: 33) |
| 8 | ADT-23 | Aaatgcaacaccggcagcggcggcagcagcctggcgaactttgatgatctggtgcatagcagcaacaac (SEQ ID NO: 34) |
| 9 | ADT-24 | Catagccagggcggcagcggcggcagcagctttgtgcagtgggatgatctgatgaac (SEQ ID NO: 35) |
| 10 | ADT-25 | Gatgcggaatttggcagcggcggcagcagcaaactggtgtttgatgattttgcggaagat (SEQ ID NO): 36) |
| 11 | ADT-31 | Gatgat (SEQ ID NO: 37) |
| 12 | ADT-32 | Gatgatgaagcgctgtatctggtgtgcggc (SEQ ID NO: 38) |
| 13 | ADT-533 | Gaagcgctgtataacaacctggtgtgcggc (SEQ ID NO: 39) |
| 14 | ADT-34 | Gaagcgctgtatgcggcgctggtgtgcggc (SEQ ID NO: 40) |
| 15 | ADT-35 | Gaagcgctgtatttttttctggtgtgcggc (SEQ ID NO: 41) |
| 16 | ADT-41 | Attaccaacccgggcagcggcggcagcagcgaagcgctgtatgatgatctggtgtgcggc (SEQ ID NO: 42) |
| 17 | ADT-42 | Attaccaacccgggcagcggcggcagcagcctggcgaactttgatgatctggtgcatagcagcaacaac (SEQ ID NO: 43) |
| 18 | ADT-43 | attaccaacccgggcagcggcggcagcagctttgtgcagtgggatgatctgatgaac (SEQ ID NO: 44) |
| 19 | ADT-44 | attaccaacccgggcagcggcggcagcagcaaactggtgtttgatgattttgcggaagat (SEQ ID NO: 45) |
| 20 | ADT-51 | tttgtgaaccagggcagcggcggcagcagcgtgctgcgctatgatgattttcataccgat SEQ ID NO: 46) |
| 21 | ADT-52 | tttgtgaaccagggcagcggcggcagcagcctggcgaactttgatgatctggtgcatagcagcaacaac (SEQ ID NO: 47) |

TABLE 3 -continued

Exemplary nucleotide sequences of peptides of some embodiments of the present invention

| No. | Peptide | Sequence 5'-3' |
|---|---|---|
| 22 | ADT-53 | tttgtgaaccagggcagcggcggcagcagctttgtgcagtgggatgatctgatgaac (SEQ ID NO: 48) |
| 23 | ADT-54 | tttgtaaccagggcagcggcggcagcagcaaactggtgtttgatgattttgcggaagat (SEQ ID NO: 49) |
| 24 | ADT-61 | aaatgcaacaccggcagcggcggcagcagcgtgctgcgctatgatgattttcataccgat (SEQ ID NO: 50) |
| 25 | ADT-62 | aaatgcaacaccggcagcggcggcagcagcgaagcgctgtatgatgatctggtgtgcggc (SEQ ID NO: 51) |
| 26 | ADT-63 | aaatgcaacaccggcagcggcggcagcagctttgtgcagtgggatgatctgatgaac (SEQ ID NO: 52) |
| 27 | ADT-64 | aaatgcaacaccggcagcggcggcagcagcaaactggtgtttgatgattttgcggaagat (SEQ ID NO: 53) |
| 28 | ADT-71 | catagccagggcggcagcggcggcagcagcgtgctgcgctatgatgattttcataccgat (SEQ ID NO: 54) |
| 29 | ADT-72 | catagccagggcggcagcggcggcagcagcgtgctgcgctatgatgattttcataccgat (SEQ ID NO: 55) |
| 30 | ADT-73 | catagccagggcggcagcggcggcagcagcctggcgaactttgatgatctggtgcatagcagcaacaac (SEQ ID NO: 56) |
| 31 | ADT-74 | catagccagggcggcagcggcggcagcagcaaactggtgtttgatgattttgcggaagat (SEQ ID NO: 57) |
| 32 | ADT-81 | gatgcggaatttggcagcggcggcagcagcgtgctgcgctatgatgattttcataccgat (SEQ ID NO: 58) |
| 33 | ADT-82 | gatgcggaatttggcagcggcggcagcagcgaagcgctgtatgatgatctggtgtgcggc (SEQ ID NO: 59) |
| 34 | ADT-83 | gatgcggaatttggcagcggcggcagcagcctggcgaactttgatgatctggtgcatagcagcaacaac (SEQ ID NO: 60) |
| 35 | ADT-84 | Gatgcggaatttggcagcggcggcagcagctttgtgcagtgggatgatctgatgaac (SEQ ID NO: 61) |

Constitutive promoters suitable for use with the present invention are promoter sequences which are active under most environmental conditions and most types of cells such as the cytomegalovirus (CMV) and Rous sarcoma virus (RSV). Inducible promoters suitable for use with the present invention include for example the tetracycline-inducible promoter (Zabala M, et al., Cancer Res. 2004, 64(8): 2799-804).

Other than containing the necessary elements for the transcription of the inserted coding sequence, the expression construct of the present invention can also include sequences engineered to enhance stability, production, purification, yield or toxicity of the expressed RNA. Recombinant synthesis is well known in the art and can also be used to synthesize the peptide in vivo using the appropriate transcription and translation elements.

In addition to being synthesizable in host cells, the peptide of the present invention can also be synthesized using in vitro expression systems. These methods are well known in the art and the components of the system are commercially available.

Following synthesis, the peptides of the present invention may optionally be tested for their IDE inhibitory activity.

Thus embodiments of the present invention also provides methods for identifying a peptide having an Insulin-degrading enzyme (IDE) inhibitory activity. The method comprising contacting IDE with a reporter substrate of the IDE in a presence or absence of the peptide, wherein a reduction in the reporter activity in the presence of the peptide is indicative of a peptide having the IDE inhibitory activity. Such a reporter substrate may be e.g. FRET (SEQ ID NO: 11), as described in detail hereinabove.

Following is a non-limiting illustration of the method.

For example, one method that may be used (as described in detail in Example 2, of the Examples section which follows) comprises the use of Insulysin/IDE Immunocapture Activity Assay Kit (available e.g. from InnoZyme™, Calbiochem). Using this kit ELISA plates are first coated with the target enzyme (i.e. IDE) and then the plates are incubated with the synthesized peptide. The enzymatic activity is measured in comparison to wells without the peptide using for example a FRET substrate, Mca-GGFLRKHGQ-EDDnp (SEQ ID NO: 11). Cleavage of the scissile amide bond between R and K releases the fluorophore from the quenching molecule, Dnp, resulting in an increase in fluorescence. The increase in fluorescence is measured using an excitation wavelength of 320 nm and an emission wavelength of 405 nm.

Due to their ability to inhibit IDE, the peptides of some aspects of the present invention can be used to treat diseases associated with IDE-activity.

As used herein a "disease associated with IDE activity" refers to a medical condition, disease or syndrome in which IDE activity contributes to onset or progression.

As previously mentioned, IDE is an enzyme which cleaves multiple small proteins of diverse sequences including insulin, amyloid β-protein (Aβ), glucagon, amylin, atrial natriuretic factor and calcitonin. Thus, in situations in which increased levels of these substrates may aid in symptom alleviation and even cure the disease, the peptides of the present invention may be employed.

It will be appreciated that the inhibitors of the present invention should not be administered in a way which allows passage through the blood brain barrier (BBB), especially in situations in which the patient has Alzheimer's disease.

Such diseases and disorders include, but are not limited to, Type 2 diabetes, Type 1 diabetes, gestational diabetes, insulin resistance, obesity, hyperglycemia, ketoacidosis, nonketotic hyperosmolar coma, viral infection (e.g. varicella-zoster virus), atherosclerosis, hypertension, cardiovascular diseases such as congenital heart defects, cardiomyopathy, aortic stenosis, atrial septal defect (ASD), atrioventricular (A-V) canal defect, ductus arteriosus, pulmonary stenosis, subaortic stenosis, ventricular septal defect (VSD), valve diseases, myocardial infraction, tuberous sclerosis, scleroderma, transplantation, endometriosis, fertility, Von Hippel-Lindau (VHL) syndrome, cirrhosis, transplantation, hemophilia, hypercoagulation, idiopathic thrombocytopenic purpura, immunodeficiencies, retinitis pigmentosa, autosomal dominant; retinitis pigmentosa, autosomal recessive; SEMD, Pakistani type; urofacial syndrome; cholesteryl ester storage disease; corneal dystrophy, Thiel-Behnke type; Dubin-Johnson syndrome; leukemia, T-cell acute lymphocytic; Leukemia, T-cell acute lymphocytic; Spinocerebellar ataxia, infantile-onset, with sensory neuropathy; Split hand/foot malformation, type 3; Tolbutamide poor metabolizer; Warfarin sensitivity; Wolman disease; anterior segment mesenchymal dysgenesis and cataract; cataract, congenital; neurofibrosarcoma, retinal damage such as nonproliferative diabetic retinopathy (NPDR) and proliferative diabetic retinopathy (PDR), chronic renal failure, diabetic nephropathy, nerve damage such as diabetic neuropathy, microvascular damage, diabetes related foot ulcers and graft versus host disease.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology. It will be appreciated that the treating may be performed alone or in conjunction with other therapies.

As used herein, the term "preventing" refers to keeping a disease, disorder or condition from occurring in a subject who may be at risk for the disease, but has not yet been diagnosed as having the disease.

It will be appreciated that the peptide of the present invention may be administered to a subject prior to onset of diabetes as a means to prevent or delay progression of the disease (see e.g. Example 4, hereinbelow).

As used herein, the term "subject" refers to a mammal, such a human being who is diagnosed, suffers or predisposed to the above mentioned medical conditions.

The peptides of the present invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the peptide accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

According to a specific embodiment of the present invention, the polypeptide of the present invention is administered via nasal administration.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multi-dose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (peptide) effective to prevent, alleviate or ameliorate symptoms of a disorder (e.g., diabetes) or prolong the survival of the subject being treated.

According to an embodiment of the present invention, administration of the peptide results in an increase in blood insulin levels of the subject.

According to another embodiment of the present invention, administration of the peptide results in an increase or maintenance of blood Insulin growth factor 1 (IGF1) levels in the subject.

According to yet another embodiment of the present invention, the administration of the peptide results in a reduction in secretion of pro-inflammatory cytokines (e.g. IFN-γ and/or IL-17) from T lymphocytes of the subject.

According to another embodiment of the present invention, administration of the peptide results in reduced autoimmune response of the subject. The autoimmune response may include for example activation, proliferation, cytokine production of T cells, including CD4+ T cells (e.g. Th1 cells, Th17 cells) and CD8+ T cells. It will be appreciated that the peptide of the present invention may reduce or ameliorate autoimmune Diabetes Type I in the subject.

According to another embodiment of the present invention, administration of the peptide results in delayed progression or prevention of diabetes.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide sufficient plasma levels of the active ingredient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

For example, according to one embodiment, a peptide of the present invention (e.g. ADT21) may be administered at a dose between 0.1-10 μg per kg body weight.

It will be appreciated that animal models exist by which the peptides of the present invention may be tested prior to human treatment. For example, Type I diabetes models include, pancreatectomy in dogs, spontaneous rodent models (e.g. BBDP rats and the NOD mice) or induction of diabetes type I by agents (e.g. streptozotocin and alloxan) which destroy pancreatic cells. Type II diabetes models and obese animal models include, db/db (diabetic) mice, Zucker diabetic fatty (ZDF) rats, sand rats (*Psammomys obesus*) and obese rhesus monkeys.

It will be appreciated that peptides of the present invention may inhibit degradation of Aβ, thus, it is important to inhibit its transfer through the blood brain barrier (BBB). Therefore in such embodiments, modalities for drug delivery through the BBB are preferably prevented. Specifically, the peptide should not be used in conjunction with BBB disruptive agents such as those which work by disruption by osmotic means, or biochemically by the use of vasoactive substances such as bradykinin, or even by localized exposure to high intensity focused ultrasound (HIFU).

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

It will be appreciated that the therapeutic compositions of the invention may comprise, in addition to the peptides, other known medications such as insulin, insulin analogs, Actos, Amaryl, Avandamet, Avandaryl, Avandia, Byetta, Cozaar, Diabeta, Diabinese, Glucophage, Glucotrol, Glucovance, Glynase, Januvia, Lantus, Metaglip, Micronase, Orinase, Prandin, Precose, Riomet, Starlix, Tolinase and Xenical. These medications may be included in the article of manufacture in a single or in separate packagings.

It is expected that during the life of a patent maturing from this application many relevant IDE inhibitory peptides will be developed and the scope of the term IDE inhibitory peptides is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Identification of IDE Inhibitory Peptides

Materials and Experimental Procedures
Rational Design of IDE Inhibitors
Multiple sequence alignments were used [ClustalW2 sequence analysis tool from EBI], for each segment separately, between the IDE known substrates: insulin B, Aβ, Amylin, Glucagon and VZV gE (UNIPROT accession numbers P01308, P05067, P10997, P01275 and P09259, respectively). For the IDE catalytic cleft binding segment, 5 sequences were compared using MSA, insulin B (37-44, SEQ ID NO: 1), Aβ (16-23, SEQ ID NO: 2), Amylin (45-55, SEQ ID NO: 3), Glucagon (74-80, SEQ ID NO: 4) and VZV gE (24-50, SEQ ID NO: 5). For the N-terminus binding segment 4 sequences were compared using MSA, insulin B chain (25-28, SEQ ID NO: 6), Amylin (34-37, SEQ ID NO: 7), Glucagon (53-56, SEQ ID NO: 8) and VZV gE (24-31, SEQ ID NO: 9). Aβ (1-4, SEQ ID NO: 10) was from the multiple sequence alignment because of its high variability compared to the other.
Results
While conceiving the present invention, it was hypothesized by the present inventors that if varicella-zoster virus (VZV) is not degraded by IDE, it may be used as a basis for IDE inhibitory peptides.

IDE is an unusual enzyme in that it possesses high affinity for substrates that are highly diverse in sequence and structure. IDE comprises two discrete segments that are clearly visible in structures in the IDE-substrate complex, where IDE substrates share similar features as shown to be true for insulin B chain, Aβ, Amylin and Glucagons (FIG. 2). The cleavage-site-containing 7-13 amino acids of all four substrates form β-sheets with IDE strands β12 and β6, respectively. IDE binding domain of VZV gE was mapped to 48 amino acids (residues 24-71, SEQ ID NO: 12) located at the amino terminus of VZV gE after its signal peptide, moreover a synthetic peptide corresponding to amino acids 24-50 of VZV gE (FIG. 2, SEQ ID NO: 5) blocked VZV gE interaction with IDE in a concentration dependent manner (data not shown).

Based on these findings the inventors tried to identify both discrete segments in VZV gE (24-50, SEQ ID NO: 5) using sequence comparison between VZV gE (24-50, SEQ ID NO: 5), and other known IDE substrates. In order to find the important amino acids for binding the IDE catalytic cleft, multiple sequence alignments of the IDE catalytic cleft binding segment of the IDE substrates to VZV gE (24-50, SEQ ID NO: 5) was preformed (FIG. 4). Catalytic cleft binding segment multiple sequence alignment (MSA) surprisingly revealed similar features between the substrates and points out the important VZV gE amino acids (Leu10, Tyr12, Phe15) that might be responsible for binding VZV gE (24-50, SEQ ID NO: 5) to the IDE catalytic cleft. Insulin B chain, Aβ, Amylin and Glucagon all share a common cleavage site, wherein in the VZV gE there are two repeats of amino acid aspartate (D) (Asp13, Asp14) instead. This repeat may change the charge in the catalytic site leading to VZV resistance to IDE, as opposed to the endogenous IDE substrates. Therefore, inventors had designed several peptides, among them one that was derived from Insulin, that may be specific for the activity of IDE (FIG. 3).

In order to find the important amino acid from the N terminus, multiple sequence alignment of the N-terminus binding segment of IDE substrates to VZV gE (24-50, SEQ ID NO: 5) was preformed (FIG. 4). Inventors had defined alignment of short peptides (4 amino acids) that contained the N-terminus binding segment of the substrates to IDE. Next, inventors combined this part with those described previously (in FIG. 2) to design segments targeting the catalytic cleft and thus to obtain increased inhibition properties (FIG. 5). Furthermore, inventors used the motif "GSGGSS"—a flexible peptide (SEQ ID NO: 13), containing Glycine and Serine, as a binding segment to allow conformation flexibility for increased probability to bind IDE (FIG. 3). Inventors have speculated that a peptide which combined IDE N-terminus binding segment plus a segment that bound IDE catalytic cleft (FIG. 3) would result as a better IDE inhibitor. These results were used as the basis for the Advanced Diabetes Therapy (ADT) platform enabling to design specific IDE inhibitors targeting the IDE Catalytic cleft (FIGS. 3 and 5).

The inventors of the present invention have thus have designed a variety of different peptides which may be used to inhibit IDE activity (see Table 4, below).

TABLE 4

IDE inhibitory peptides

| No. | Peptide | Amino acid sequence |
|---|---|---|
| 1 | ADT-1 | VLRYDDFHTD (SEQ ID NO: 14) |
| 2 | ADT-2 | EALYDDLVCG (SEQ ID NO: 15) |

TABLE 4 -continued

IDE inhibitory peptides

| No. | Peptide | Amino acid sequence |
|---|---|---|
| 3 | ADT-3 | LANFDDLVHSSNN (SEQ ID NO: 16) |
| 4 | ADT-4 | FVQWDDLMN (SEQ ID NO: 17) |
| 5 | ADT-5 | KLVFDDFAED (SEQ ID NO: 18) |
| 6 | ADT-21 | ITNPGSGGSSVLRYDDFHTD (SEQ ID NO: 19) |
| 7 | ADT-22 | FVNQGSGGSSEALYDDLVCG (SEQ ID NO: 20) |
| 8 | ADT-23 | KCNTGSGGSSLANFDDLVHSSNN (SEQ ID NO: 21) |
| 9 | ADT-24 | HSQGSGGSSFVQWDDLMN (SEQ ID NO: 22) |
| 10 | ADT-25 | DAEFGSGGSSKLVFDDFAED (SEQ ID NO: 23) |
| 11 | ADT-31 | DD (SEQ ID NO: 26) |
| 12 | ADT-32 | DDEALYLVCG (SEQ ID NO: 62) |
| 13 | ADT-33 | EALYNNLVCG (SEQ ID NO: 63) |
| 14 | ADT-34 | EALYAALVCG (SEQ ID NO: 64) |
| 15 | ADT-35 | EALYFFLVCG (SEQ ID NO: 65) |
| 16 | ADT-36 | EALYEELVCG (SEQ ID NO: 66) |
| 17 | ADT-41 | ITNPGSGGSSEALYDDLVCG (SEQ ID NO: 67) |
| 18 | ADT-42 | ITNPGSGGSSLANFDDLVHSSNN (SEQ ID NO: 68) |
| 19 | ADT-43 | ITNPGSGGSSFVQWDDLMN (SEQ ID NO: 69) |
| 209 | ADT-44 | ITNPGSGGSSKLVFDDFAED (SEQ ID NO: 70) |
| 21 | ADT-51 | FVNQGSGGSSVLRYDDFHTD (SEQ ID NO: 71) |
| 22 | ADT-52 | FVNQGSGGSSLANFDDLVHSSNN (SEQ ID NO: 72) |
| 23 | ADT-53 | FVNQGSGGSSFVQWDDLMN (SEQ ID NO: 73) |
| 24 | ADT-54 | FVNQGSGGSSKLVFDDFAED (SEQ ID NO: 74) |
| 25 | ADT-61 | KCNTGSGGSSVLRYDDFHTD (SEQ ID NO: 75) |
| 26 | ADT-62 | KCNTGSGGSSEALYDDLVCG (SEQ ID NO: 76) |
| 27 | ADT-63 | KCNTGSGGSSFVQWDDLMN (SEQ ID NO: 77) |
| 28 | ADT-64 | KCNTGSGGSSKLVFDDFAED (SEQ ID NO: 78) |
| 29 | ADT-71 | HSQGSGGSSVLRYDDFHTD (SEQ ID NO: 79) |
| 30 | ADT-72 | HSQGSGGSSEALYDDLVCG (SEQ ID NO: 80) |
| 31 | ADT-73 | HSQGSGGSSLANFDDLVHSSNN (SEQ ID NO: 81) |
| 32 | ADT-74 | HSQGSGGSSKLVFDDFAED (SEQ ID NO: 82) |
| 33 | ADT-81 | DAEFGSGGSSVLRYDDFHTD (SEQ ID NO: 83) |
| 34 | ADT-82 | DAEFGSGGSSEALYDDLVCG (SEQ ID NO: 84) |
| 35 | ADT-83 | DAEFGSGGSSLANFDDLVHSSNN (SEQ ID NO: 85) |
| 36 | ADT-84 | DAEFGSGGSSFVQWDDLMN (SEQ ID NO: 86) |

Example 2

Effect of the Insulin Degrading Enzyme (IDE) Inhibitor on IDE Activity

Materials and Experimental Procedures

Analysis of Insulin Degrading Enzyme (IDE) Activity (Fluorometric IDE Activity Assay)

In order to measure IDE activity, coating of ELISA plates with the target enzyme (i.e. IDE) was carried out. Next, plates were incubated with the selected synthesized peptide candidate and the enzymatic activity was measured as compared to wells without the peptide candidate. This was carried out using InnoZyme™ Insulysin/IDE Immunocapture Activity Assay Kit from Calbiochem (worldwidewebdotmerckbiosciencesdotcom/Products/pdsdotaspquestionmarkcatnoequal CBA079), a specific and sensitive assay for measuring active IDE in cell lysates, tissue extracts and biological fluids.

Peptide ability to inhibit IDE activity was measured using InnoZyme™ Insulysin/IDE Immunocapture activity assay kit (Calbiochem), an affinity purified polyclonal antibody that recognized human, mouse, and rat insulysin, immobilized on a 96-well plate to capture the enzyme. In brief, rat recombinant IDE (1.14 nM) was incubated with increasing amounts of the candidate inhibitors with doses ranging from 1-100 µM for 16 hours at 37° C. and the activity of captured IDE was measured using a FRET substrate, Mca-GGFLRKHGQ-EDDnp (SEQ ID NO: 11). Cleavage of the scissile amide bond between R and K released the fluorophore from the quenching molecule, Dnp, resulting in an increase in fluorescence. The increase in fluorescence was measured using an excitation wavelength of 320 nm and an emission wavelength of 405 nm. As a control, the kit used rat recombinant IDE. IC50 were evaluated following three repeated experiments.

Results

Inventors of the present invention investigated the designed ADT platform using the InnoZyme™ Insulysin/IDE Immunocapture Activity Assay Kit which was designed to measure IDE activity in cell lysates, tissue extracts, and biological fluids from human, mouse and rat samples. Rat recombinant IDE was used for control. A series of IDE peptide inhibitors were synthesized and tested for inhibition of IDE activity and insulin degradation. As depicted in Table 5 (hereinbelow), IDE inhibitors inhibited IDE activity in a dose dependant manner.

Specifically, rat recombinant IDE (1.14 nM) was incubated with different doses of ADT-21 (0-100 mM) for 16 hours at 37° C. and the activity of the captured insulysin (IDE) was measured using a FRET substrate, Mca-GGFLRKHGQ-EDDnp (SEQ ID NO: 11) using Florolog with the following parameters Ex=320 nm, Gm=405 nm, Slit=2, Maximum trails=10, Integration time=1, Target standard deviation=1%.

Figure 6:
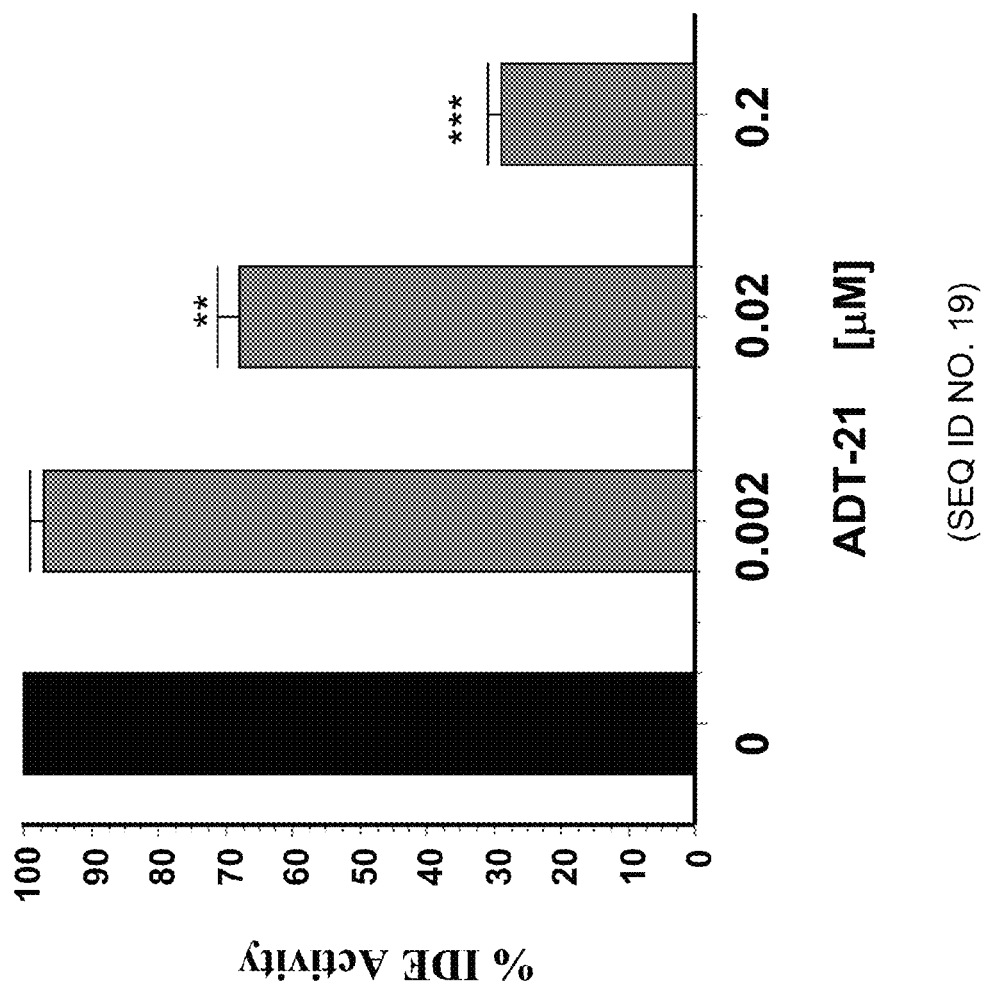

The inventors have surprisingly found that in using ADT-21 a dose dependent and high efficacy in inhibition of IDE activity was achieved (Table 5 and FIG. 6, IC50=100 nM, p<0.0001). This inhibitor was based on the original VZV amino acid residues which bind to IDE (FIG. 2) and included the N-Terminal amino acids (FIG. 4) and the motif "GSGGSS" (SEQ ID NO: 13).

Furthermore, as indicated in Table 5, inserting the motif DD (SEQ ID NO: 26) increased the IC50 of the insulin derived peptide (INS) from 465 to 230 nM (ADT2). Moreover, combining the N-terminus binding segments (FIG. 4) with the segments that target the catalytic cleft of each target (FIG. 2) along with the motif "GSGGSS" (SEQ ID NO: 13) improved IC50 values [Table 5, below, e.g. comparison between VZV (No. 5) and ADT21 (No. 6)]. Changing the side of the insert to form an aromatic sequence (as in NN, ADT5N) prevented the inhibition of IDE. The motif DD by itself displayed an IC50 of 736 nM. From these experiments, inventors concluded that inserting the motif DD was important for modulation of IDE inhibitors.

TABLE 5

IC50 of ADT inhibitors

| No. | Peptide Name | Sequence | IC50 (nM) |
|---|---|---|---|
| 1 | ADT1 | VLRYDDFHTD (SEQ ID NO: 14) | 145 |
| 3 | ADT5N | VLRYNNFHTD (SEQ ID NO: 87) | — |
| 4 | ADT-31 | DD (SEQ ID NO: 26) | 736 |
| 5 | VZV | ITNPVRASVLRYDDFHTD (SEQ ID NO: 88) | 450 |
| 6 | ADT21 | ITNPGSGGSSVLRYDDFHTD (SEQ ID NO: 19) | 100 |
| 7 | ADT51 | FVNQGSGGSSVLRYDDFHTD (SEQ ID NO: 71) | 494 |
| 8 | ADT61 | KCNTGSGGSSVLRYDDFHTD (SEQ ID NO: 75) | 824 |
| 9 | ADT71 | HSQGGSGGSSVLRYDDFHTD (SEQ ID NO: 79) | 1386 |
| 10 | INS | EALYLVCG (SEQ ID NO: 1) | 465 |
| 11 | ADT2 | EALYDDLVCG (SEQ ID NO: 15) | 230 |
| 12 | ADT41 | ITNPGSGGSSEALYDDLVCG (SEQ ID NO: 67) | 331 |
| 13 | ADT72 | HSQGGSGGSSEALYDDLVCG (SEQ ID NO: 80) | 118 |
| 14 | ADT82 | DAEFGSGGSSEALYDDLVCG (SEQ ID NO: 84) | 438 |
| 15 | ADT62 | KCNTGSGGSSEALYDDLVCG (SEQ ID NO: 76) | 713 |
| 16 | ADT22 | FVNQGSGGSSEALYDDLVCG (SEQ ID NO: 20) | — |
| 17 | ADT3 | LANFDDLVHSSNN (SEQ ID NO: 16) | 788 |
| 18 | ADT23 | KCNTGSGGSSLANFDDLVHSSNN (SEQ ID NO: 21) | 616 |
| 19 | ADT42 | ITNPGSGGSSLANFDDLVHSSNN (SEQ ID NO: 68) | 199 |
| 20 | ADT52 | FVNQGSGGSSLANFDDLVHSSNN (SEQ ID NO: 72) | — |
| 21 | ADT4 | FVQWDDLMN (SEQ ID NO: 17) | — |
| 22 | ADT43 | ITNPGSGGSSFVQWDDLMN (SEQ ID NO: 69) | — |
| 23 | ADT24 | HSQGGSGGSSFVQWDDLMN (SEQ ID NO: 22) | 175 |
| 24 | ADT5 | KLVFDDFAED (SEQ ID NO: 18) | 552 |
| 25 | ADT44 | ITNPGSGGSSKLVFDDFAED (SEQ ID NO: 70) | 545 |

TABLE 5 -continued

IC50 of ADT inhibitors

| No. | Peptide Name | Sequence | IC50 (nM) |
|---|---|---|---|
| 26 | ADT25 | DAEFGSGGSSKLVFDDFAED (SEQ ID NO: 23) | 604 |

Each IC50 is based on 3 repeated experiments

Example 3

ADT21 Inhibits Insulin Degradation by IDE

Figure 7:
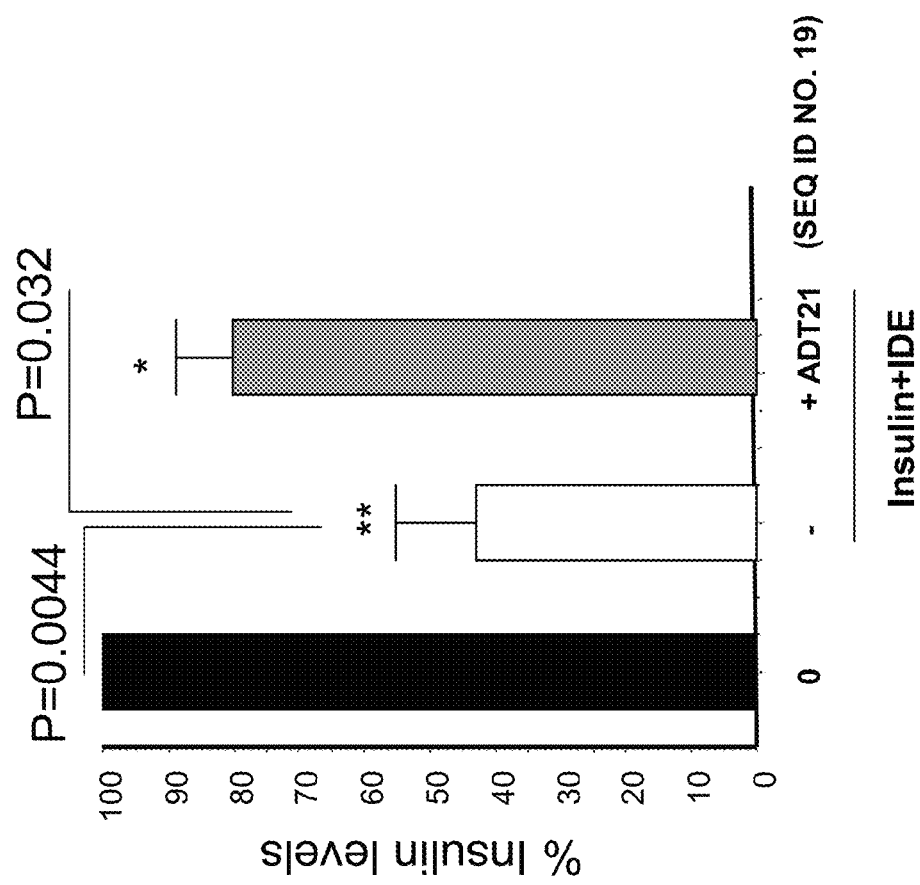

Materials and Experimental Procedures
In Vitro Insulin Degradation Assay
Insulin (0.87 nM) isolated from bovine pancreas (SIGMA) was incubated for 16 hours at 37° C. in the presence or absence of IDE (1.14 nM) together with the inhibitors (0.002-0.2 nM). The levels of insulin degradation were analyzed using mouse insulin ELISA kit (Mercodia).
Results
In order to verify that ADT21 reduces degradation of insulin by IDE, inventors incubated bovine insulin for 16 hours at 37° C. with or without IDE (1.14 nM) along with ADT21. The levels of insulin degradation were analyzed using a mouse insulin ELISA kit (as described in the "materials and experimental procedures" section above). As shown in FIG. 7, ADT21 (0.2 nM) reduced insulin degradation by 400% (from 60% to only 20% degradation). These results suggested that while the inhibitor significantly reduced insulin degradation, it did not completely block IDE activity. Therefore, inventors speculated that the use of this inhibitor in vivo would delay insulin degradation without preventing IDE activity.

Example 4

Figure 8:
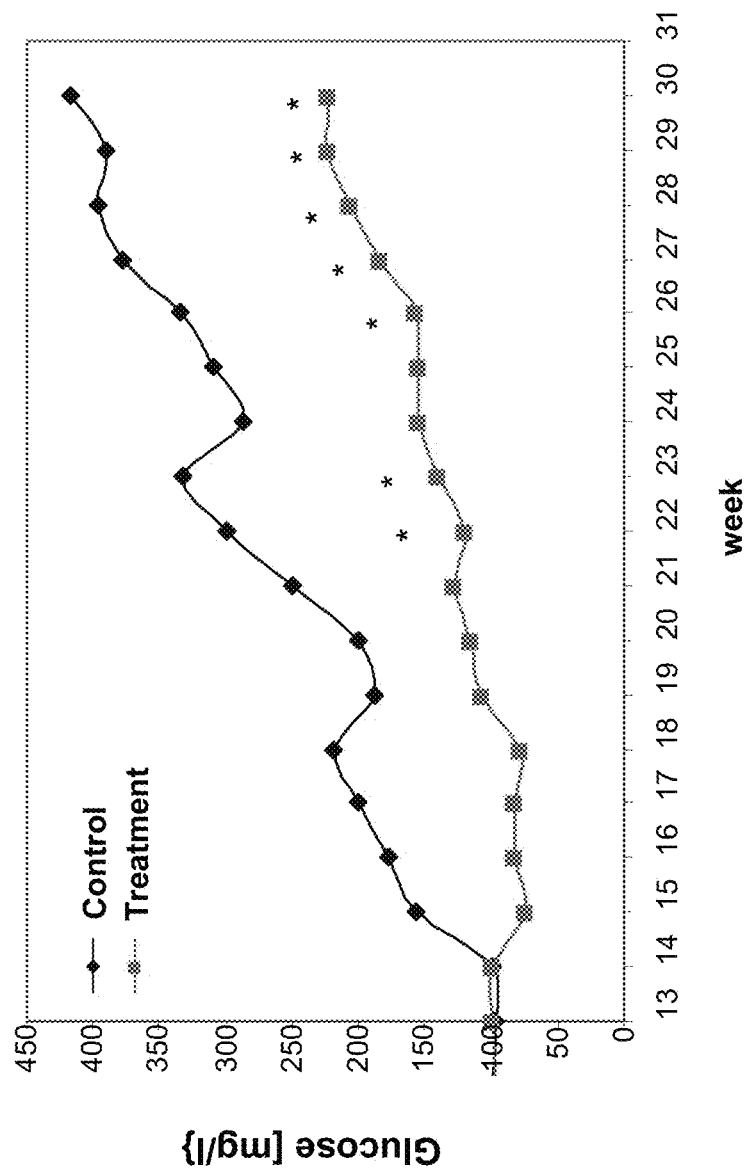
Figure 9:
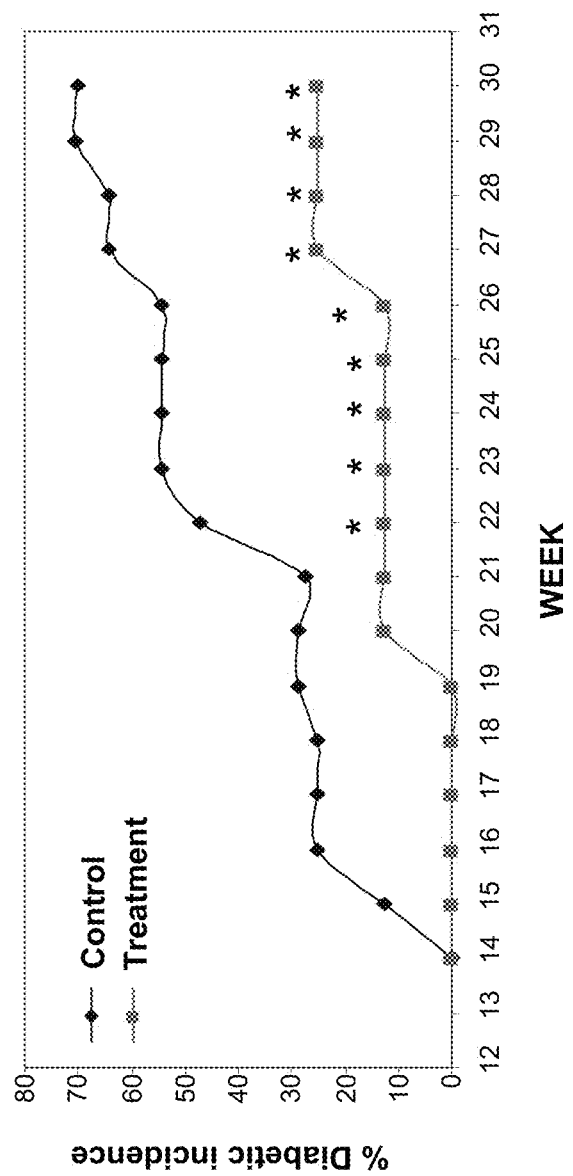
Figure 10:
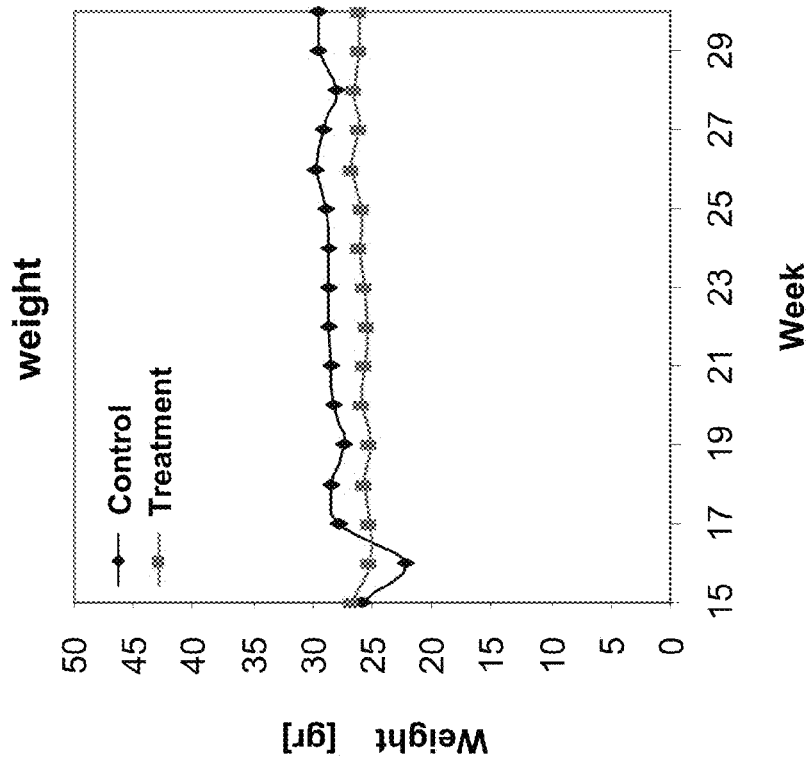

In Vivo Treatment of NOD Mice with ADT21 Decreased Insulitis and Delayed Onset of Diabetes Materials and Experimental Procedures
Diabetic Mouse Model
A NOD mouse model has been used as previously described as a model for insulin dependent diabetes mellitus (IDDM) [Atkinson et al., (1990) Diabetes 39, 933-937]. Diabetes in NOD (NOD/ShiLtJ) mice is characterized by insulitis and marked decreases in pancreatic insulin content that occurred in females at about 15 weeks of age. The animals were monitored carefully when receiving the different treatments. Onset of diabetes was marked by moderate glycosuria and by non-fasting plasma glucose higher than 250 mg/dl.
Nasal Administration
12 week old NOD mice were divided into two groups of 10-12 mice each, receiving, every other day, nasal administration of 10 µl of the respective peptide (3.76 µg/kg) or control PBS.
Glucose Levels
Mice were monitored for blood glucose levels weekly using glucose test strip (Elite, BAYER).
Insulin Levels
Mice were monitored for insulin blood levels at 30 week using HTRF® Insulin assay (Cisbio bioassays).
Results
Inventors hypothesized that in vivo treatment of NOD mice with ADT21 would delay insulin degradation by IDE, which would help control elevation of blood glucose levels leading to diabetes. To test this hypothesis, 12-week-old pre-diabetic NOD mice were treated with either ADT21 (94 ng/day) or PBS every other day and monitored for diabetes progression (FIGS. 8-9). The first of the untreated NOD mice became diabetic at 15 weeks of age (FIG. 9). At 30 weeks, 71% of control mice had developed diabetes (glucose level higher then 300 mg/l). In contrast, in the ADT21-treated group, disease progression was significantly delayed (P<0.05). The first conversion to diabetes in the ADT21-treated group did not occur until 20 weeks of age, and 75% of the animals remained disease-free at 30 weeks (P<0.05). The ADT21-treated animals exhibited no behavioral changes, as measured by body weight (FIG. 10), eating habits, tail tone, or mobility that might indicate toxicity.

Figure 11:
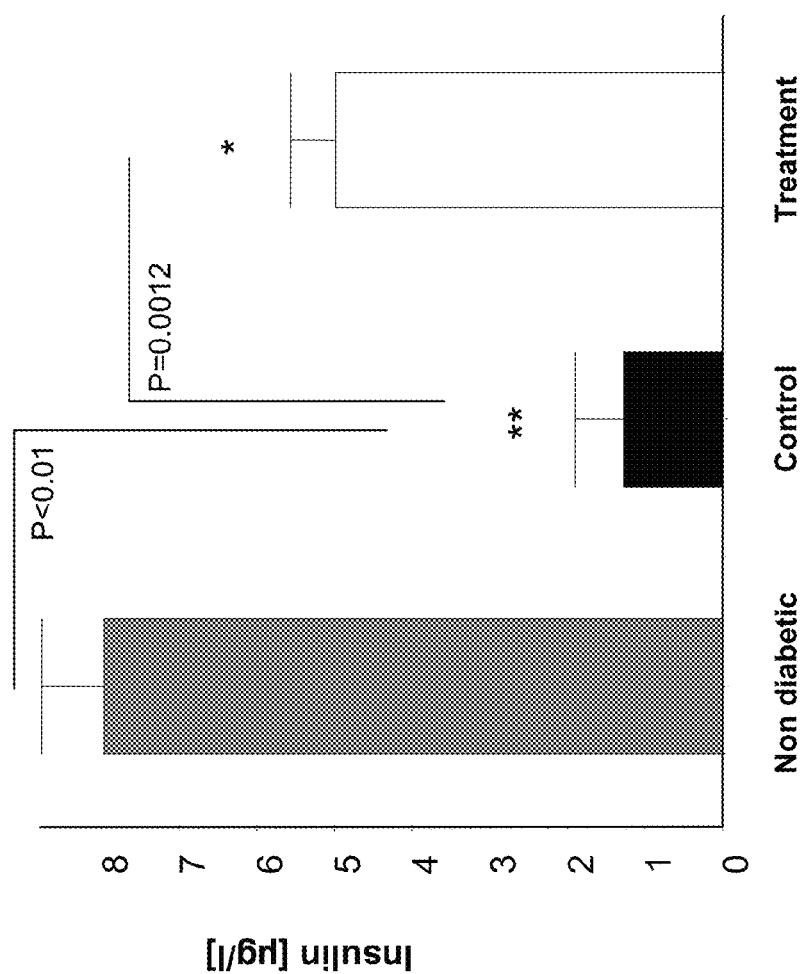

In order to assess that the difference between the treated group and the control group was related to higher blood insulin levels, inventors bled the mice at 30 weeks of age and tested the level of insulin in the serum. Inventors discovered (FIG. 11) that while in the control group there was 84% reduction in insulin compared to non diabetic NOD mice (age 12 weeks), the ADT21 treatment yielded an increase of about 400% in the blood insulin, to a level of 62% compared to sick NOD mice (p=0.0012).

Example 5

Nasal ADT21 Reduced Cellular Infiltrate of Pancreatic Islets in NOD Mice

Materials and Experimental Procedures
Diabetic Mouse Model
As described in Example 4, above.
Nasal Administration
As described in Example 4, above.
Degree of Insulitis Randomly selected animals from each group (at 30 weeks) were sacrificed and the pancreas of each was examined in a double-blind fashion for insulitis using histological analysis of the pancreas as previously described [Frenkel et al. (2003) J Immunol 171, 6549-6555]. Six to ten islets per mouse were individually scored by two independent observers using a semi-quantitative scale ranging from 0-4 as follows: 0, normal islet with no sign of T cell infiltration; 1, islet associated with perivascular, periductal leukocytic infiltration only; 2, more extensive peri-islet infiltration, but with lymphocytes with less than 25% islet destruction; 3 more than 25% islet destruction; and 4, complete islet destruction.

Results

Figure 12:
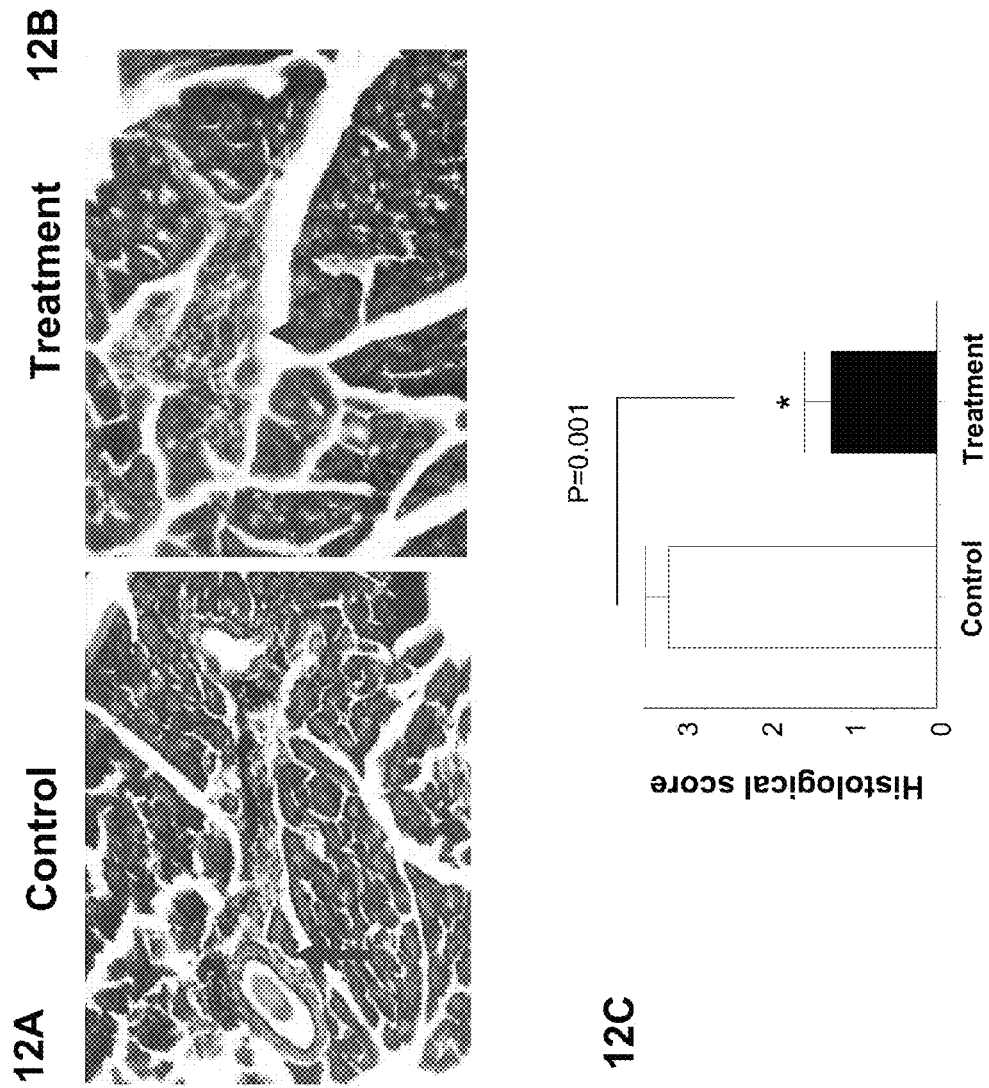

Randomly selected mice were sacrificed at the age of 30 weeks, at the end of the treatment, and compared to PBS treated mice. As shown in the FIGS. 12A-C (representative histology for each of these groups is shown in FIGS. 12A-B and insulitis scores in these mice is shown in FIG. 12C), there was significantly less infiltration of T cells in mice treated with ADT21 compared with the PBS-treated group. Furthermore, in the control group there was significantly higher evidence of islet destruction as shown in FIG. 12A.

Example 6

ADT21 Treatment Lead to Increased IGF-1 in the Serum of NOD Mice

Materials and Experimental Procedures
Diabetic Mouse Model
As described in Example 4, above.
Nasal Administration
As described in Example 4, above.
IGF-1 Level NOD mice were monitored for the blood level of Insulin growth factor 1 (IGF-1) at 30 weeks using AssayMax mouse IGF1 kit.

Results

Figure 13:
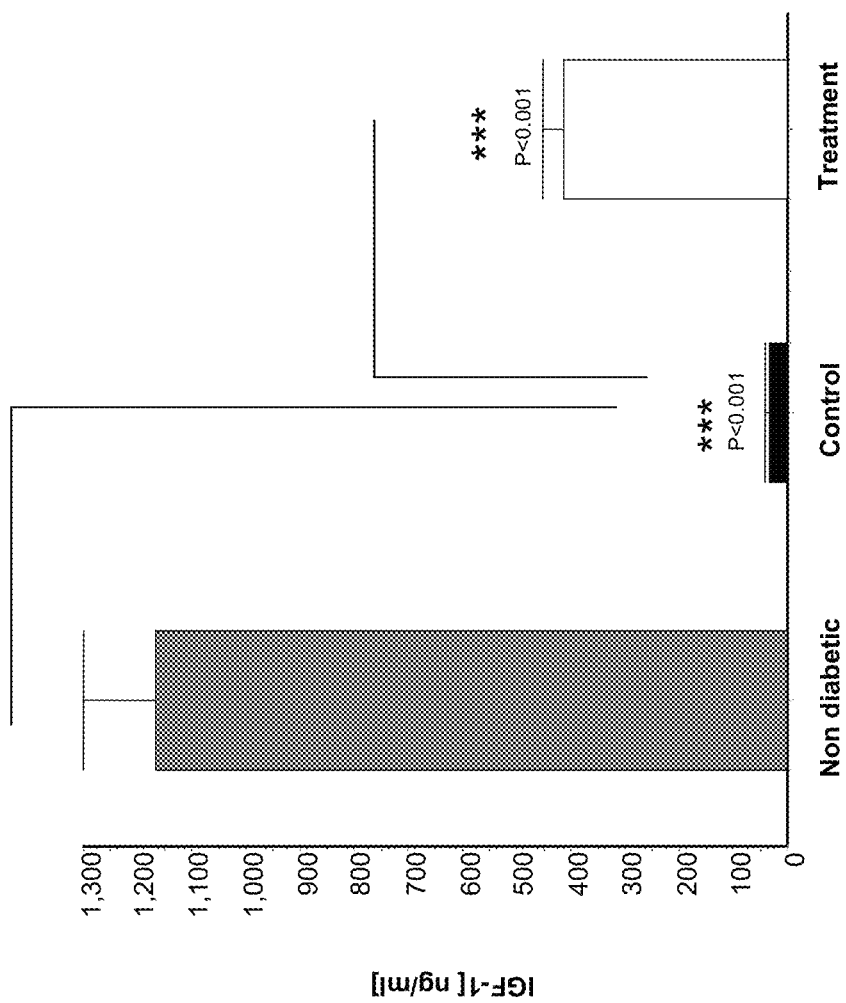

Diabetes affects many systems of the body. Complicated diabetic patients show delayed wound healing caused by multiple factors including vascular insufficiency, abnormalities of the biochemical environment and hyperglycemia. Chronic wounds fail to progress through the normal stages of healing, and enter a state of pathologic inflammation. Analysis of growth factor expression previously showed a marked reduction in insulin-like growth factor-1 (IGF1) in diabetic wounds [Yu et al. (2007) Wound Repair Regen 15, 628-635]. Inventors investigated how treatment of diabetic mice with ADT21 affected the levels of IGF1 (which is also another IDE substrate) as compared to control mice. As shown in FIG. 13, ADT21 treatment lead to an increase in IGF1 blood levels from 33 ng/ml (control NOD mice group) to 440 ng/ml (p<0.001, ADT21 treated group). While IGF1 treatment may lead to toxic elevation above a basal level (about 1000 ng/ml in wild type mice), the current treatment was below the basal level and therefore no toxic effect was observed.

Example 7

Nasal ADT21 Reduces IL-17 and IFN-γ Secretion Levels from T Cells Obtained from ADT21-Treated NOD Mice Materials and Experimental Procedures
Diabetic Mouse Model
As described in Example 4, above.
Nasal Administration
As described in Example 4, above.
Splenocyte Culture Splenocytes were obtained from NOD mice at the age of 30 weeks. Splenocytes were obtained from both control and ADT21-treated mice. Splenocytes were cultured in T cell medium buffer and plated at $1\times10^6$ cells per well with and without bovine insulin (Sigma) for 48 hours as previously described [Frenkel et al. (2003) J Immunol 171, 6549-6555].

ELISA for Cytokines

Secretions of IFN-γ and IL-17 were measured in 48 hour cultured supernatants by ELISA. Briefly, 96 well plates were coated overnight with 1.5 µg/ml capture antibody (R&D Systems). Supernatants (as described above) were incubated overnight and detection biotinylated antibody (1 µg/ml, R&D Systems) was added for 1 hour. Plates were covered for 30 minutes with avidin-HRP conjugate and TNB was used as a substrate for color development. 1M $H_2SO_4$ was used as a stop solution. Plates were measured using an ELISA plate reader at 405 nm.

Results

The T helper 17 (Th17) population, a subset of CD4-positive T-cells that secrete interleukin (IL)-17, has been implicated in autoimmune diseases, including multiple sclerosis and lupus. Recent research suggested that Th1 cells [Eur J Immunol. (2009) January; 39(1):216-24] and Th17 cells [Diabetes (2009) June; 58(6):1302-11] are involved in the pathogenesis of autoimmune diabetes. Therefore, development of Th1 and/or Th17-targeted therapeutic agents may be of benefit in this disease. In order to investigate the effect of ADT21 on the levels of IFN-γ and IL-17 secretion from these cells, splenocytes were incubated with insulin and after 48 hours the levels of IFN-γ and IL-17 secreted from these cells was measured. As shown in FIG. 14B, a 52% reduction in the levels of IL-17 was observed in cells obtained from ADT21-treated mice. Similar results were obtained in secretion of IFN-γ from cells obtained from ADT21-treated mice (FIG. 14A). Taken together, these results suggest that ADT21 reduces Th1 and Th17 activity and IFN-γ and IL-17 secretion leading to a significant reduction in disease occurrence between treated and control diabetic mice.

Example 8

ADT21 Reduces IL-17 and IFN-γ Secretion from Activated T Cells

Materials and Experimental Procedures
Diabetic Mouse Model
As described in Example 4, above.
Co-Culture Protocol
NOD mice were immunized subcutaneously (s.c.) with bovine insulin (SIGMA) (n=6-7). 10 days later, CD4+ T-cells were isolated from the spleens of these mice using magnetic beads for negative selection (Miltenyi Biotec). The CD4+ T cells were co-cultured at a concentration of $1 \times 10^6$ cells/well in 96-well plates at a ratio of 1:1 with cells obtained from spleens of non immunized NOD mice (n=5). The co-culture was incubated with 10 μg/ml insulin with or without 100 nM ADT21. Supernatants were collect after 48 h of co-culture for cytokine measurements by ELISA for IL-17 and IFN-γ.
ELISA for Cytokines
As described in Example 7, above.
Results
In order to investigate the importance of IDE as therapeutic target for use in reducing autoimmune CD4+ T-cell proliferation in type I diabetics, inventors established a co-culture of CD4+ T-cells (obtained from NOD mice immunized with insulin) and macrophages (obtained from spleens of non immunized NOD mice) as described in the materials and method section above. The cells in the co-culture were incubated with insulin in the presence or absence of the IDE inhibitor, ADT21. As shown in FIGS. 15A-B, following incubation with ADT21, a dose dependant reduction in the release of the pro inflammatory Th1 CD4+ T-cell cytokine IFN-γ ($p<0.01$) and the pro inflammatory Th17 CD4+ T-cell cytokine IL-17 ($p<0.05$) was observed.

Example 9

Reduced Secretion of Pro-Inflammatory Cytokines in $IDE^{-/-}$ Mice

Materials and Experimental Procedures
$IDE^{-/-}$ Mouse Model
10 weeks $IDE^{-/-}$ mice from a C57BL/6 background and 10 weeks old C57BL/6 mice (wild type) were immunized s.c. with bovine insulin (SIGMA) (n=7). 10 days later, splenocytes were isolated from spleens of these mice. The splenocytes were cultured at a concentration of $1 \times 10^6$ cells/well in 96-well plates and incubated with 10 μg/ml insulin. Supernatants were collect after 48 h of co-culture for cytokine measurements by ELISA for IL-17 and IFN-γ.
ELISA for Cytokines
As described in Example 7, above.
Results
In order to investigate the role of IDE in mediating T-cell proliferation and activation in type I diabetes, inventors immunized WT and $IDE^{-/-}$ mice with insulin and isolated their spleens to investigate the level of the immune response. As shown in FIGS. 16A-B, a significant decrease in pro-inflammatory cytokine production was evident in $IDE^{-/-}$ mice. Both Th1 (IFN-g) and Th17 (IL-17) pro-inflammatory response was higher in NOD mice as compared to WT and $IDE^{-/-}$ mice (data not shown).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a disease selected from the group consisting of diabetes, obesity, hyperglycemia, proliferative diabetic retinopathy, diabetic nephropathy, diabetic neuropathy and varicella-zoster virus (VZV) infection in a subject in need thereof, the method comprising administering to the subject a therapeutically effective amount of an isolated peptide comprising the amino acid sequence as set forth in SEQ ID NO: 19, the peptide being no more than 25 amino acids in length.

2. An isolated peptide comprising the amino acid sequence as set forth in SEQ ID NO: 19 the peptide being no more than 25 amino acids in length.

3. The method of claim 1, wherein the peptide is as set forth in SEQ ID NO: 19.

4. A pharmaceutical composition comprising as an active ingredient the isolated peptide of claim 2 and a pharmaceutically acceptable carrier.

5. An article of manufacture comprising the isolated peptide of claim 2 and insulin each being packaged in a packaging material and identified in print, in or on said packaging material for use in the treatment of diabetes.

6. A method of identifying a peptide having an Insulin-degrading enzyme (IDE) inhibitory activity, the method comprising: contacting IDE with a reporter substrate of said IDE in a presence of the peptide of claim 2, wherein a reduction in said reporter activity in the presence of said peptide is indicative of a peptide having the IDE inhibitory activity.

7. The method of claim 1, wherein said therapeutically effective amount is between 0.1-10 μg per kg body weight.

8. An isolated peptide comprising the amino acid sequence of SEQ ID NO: 19.

9. The method of claim 1, wherein the peptide is no more than 20 amino acids in length.

10. The isolated peptide of claim 2, being no more than 20 amino acids in length.

11. The isolated peptide of claim 2, consisting of SEQ ID NO:19.

* * * * *